United States Patent
Chen et al.

(10) Patent No.: US 9,580,379 B2
(45) Date of Patent: *Feb. 28, 2017

(54) XANTHINE OXIDASE INHIBITORS AND METHODS OF USE

(71) Applicant: Baylor College of Medicine, Houston, TX (US)

(72) Inventors: Changyi Chen, Houston, TX (US); Qizhi Yao, Houston, TX (US); Jian-Ming Lu, Pearland, TX (US)

(73) Assignee: BAYLOR COLLEGE OF MEDICINE, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/508,960

(22) Filed: Oct. 7, 2014

(65) Prior Publication Data

US 2015/0353471 A1 Dec. 10, 2015

Related U.S. Application Data

(60) Provisional application No. 61/996,964, filed on Jun. 9, 2014.

(51) Int. Cl.
| | | |
|---|---|---|
| A61K 31/11 | (2006.01) | |
| C07C 205/37 | (2006.01) | |
| C07C 323/16 | (2006.01) | |
| C07C 217/58 | (2006.01) | |
| C07D 317/62 | (2006.01) | |
| C07D 317/64 | (2006.01) | |
| C07F 9/12 | (2006.01) | |
| A61K 31/09 | (2006.01) | |
| A61K 31/137 | (2006.01) | |
| A61K 31/222 | (2006.01) | |
| A61K 31/275 | (2006.01) | |
| A61K 31/357 | (2006.01) | |
| A61K 31/385 | (2006.01) | |
| A61K 31/4166 | (2006.01) | |
| A61K 31/426 | (2006.01) | |
| A61K 31/661 | (2006.01) | |
| C07C 305/24 | (2006.01) | |
| C07C 207/04 | (2006.01) | |
| C07C 239/12 | (2006.01) | |
| C07F 7/18 | (2006.01) | |
| C07C 205/43 | (2006.01) | |
| C07C 205/44 | (2006.01) | |
| C07C 251/48 | (2006.01) | |

(52) U.S. Cl.
CPC ............ *C07C 205/37* (2013.01); *A61K 31/09* (2013.01); *A61K 31/11* (2013.01); *A61K 31/137* (2013.01); *A61K 31/222* (2013.01); *A61K 31/275* (2013.01); *A61K 31/357* (2013.01); *A61K 31/385* (2013.01); *A61K 31/4166* (2013.01); *A61K 31/426* (2013.01); *A61K 31/661* (2013.01); *C07C 207/04* (2013.01); *C07C 217/58* (2013.01); *C07C 239/12* (2013.01); *C07C 305/24* (2013.01); *C07C 323/16* (2013.01); *C07D 317/62* (2013.01); *C07D 317/64* (2013.01); *C07F 7/1852* (2013.01); *C07F 9/12* (2013.01); *C07C 205/43* (2013.01); *C07C 205/44* (2013.01); *C07C 251/48* (2013.01)

(58) Field of Classification Search
USPC .......................................................... 514/699
See application file for complete search history.

(56) References Cited

U.S. PATENT DOCUMENTS

| | | | |
|---|---|---|---|
| 5,308,840 A | 5/1994 | Sugiyama et al. | |
| 8,883,858 B1 * | 11/2014 | Chen ....................... | C07C 47/54 514/699 |
| 8,895,626 B1 * | 11/2014 | Chen ....................... | C07C 47/54 514/699 |

OTHER PUBLICATIONS

Lu et al., "3,4-Dihydroxy-5-nitrobenzaldehyde (DHNB) is a Potent Inhibitor of Xanthine Oxidase a potential therapeutic agent for treatment of hyperuricemia and gout," BioChem. Pharmacol., (2013), vol. 86(9):22 pgs (Especially: p. 2, para 3; p. 2, Para 4; p. 14, Figure 1, DHNB.
PCT International Search Report and Written opinion dated Jan. 27, 2016 in PCT Application No. PCT/US2015/034970.

* cited by examiner

*Primary Examiner* — Rei-Tsang Shiao
(74) *Attorney, Agent, or Firm* — Foley & Lardner LLP

(57) ABSTRACT

Small molecule xanthine oxidase inhibitors are provided, as well as compositions, methods for their use for treating disorders, mediated at least in part, by xanthine oxidase.

9 Claims, 14 Drawing Sheets

XANTHINE OXIDASE INHIBITORS AND METHODS OF USE

CROSS-REFERENCE TO RELATED APPLICATIONS

This application claims the benefit under 35 U.S.C. §119 (e) to U.S. provisional application Ser. No. 61/996,964, which was concurrently converted herewith from U.S. nonprovisional application Ser. No. 14/300,056, filed Jun. 9, 2014, which are incorporated hereby by reference in their entirety.

BACKGROUND OF THE INVENTION

Field of the Invention

This invention is directed to compounds, pharmaceutical compositions and methods. The methods of this invention are useful in treating a condition mediated at least in part by xanthine oxidase including by way of example, gout, hyperuricemia, hypoxia and the like.

State of the Art

Gout is caused by hyperuricemia, namely, abnormally high levels of uric acid in the blood. Gout is usually presented as acute inflammatory arthritis, as well as tophi, kidney stones, or urate nephropathy. Gout affects 1-2% of adults in developed countries and represents the most common case of inflammatory arthritis in men. In the United States, gouty arthritis accounts for millions of outpatient visits annually. Furthermore, gout and hyperuricemia are also associated with chronic diseases such as hypertension, diabetes mellitus, metabolic syndrome, and renal and cardiovascular disease.

Xanthine oxidase (XO) is a form of a molybdoflavin protein, xanthine oxidoreductase (XOR). It plays an important role in the catabolism of purines in humans, as it catalyzes the oxidation of hypoxanthine to xanthine and then catalyzes the oxidation of xanthine to uric acid. Meanwhile, reactive oxygen species (ROS), including superoxide and $H_2O_2$, are generated during this process. In a bioprotective role, uric acid can serve as an antioxidant to prevent macromolecular damage by ROS. However, overproduction of uric acid causes hyperuricemia which can lead to gout and other diseases or conditions. Therefore, maintaining uric acid at normal levels represents an important therapeutic goal for the prevention of gout and related disorders. For most patients with primary gout, the condition is directly related to the overproduction of uric acid (hyperuricemia).

Currently, two drugs have been developed to treat gout. Allopurinol is the most commonly used therapy for chronic gout and has been used clinically for more than 40 years. Allopurinol lowers uric acid production by inhibiting XO activity, and is used as a first-line urate-lowering phamacotherapy. Allopurinol, a structural isomer of hypoxanthine, is hydroxylated by XO to oxypurinol, which coordinates tightly to the reduced form of the molybdenum center, replacing the Mo—OH group of the native enzyme. Unfortunately, while rare, allopurinol has life-threatening side effects such as a hypersensitivity syndrome consisting of fever, skin rash, eosinophilia, hepatitis, and renal toxicity, for which the mortality rate approaches 20%. It also causes Stevens-Johnson syndrome (SJS) and toxic epidermal necrolysis (TENS), two life-threatening dermatological conditions. Febuxostat, a non-purine xanthine oxidase inhibitor, has been approved for the management of gout in Europe and the United States. Side effects are also found with this drug including elevated serum liver enzymes, nausea, diarrhea, arthralgia, headache, and rash.

Notwithstanding the need for drugs with improved safety in the treatment of gout, hyperuricemia, and related disorders, drugs available for treatment and prevention of such disorders remain limited. Therefore, safe and effective xanthine oxidase inhibitors are needed for treating such disorders.

SUMMARY OF THE INVENTION

This invention is directed to compounds, pharmaceutical compositions, and methods of use in order to treat disorders mediated, at least in part, by xanthine oxidase. This invention is also directed to methods for treating, for example, hypoxia, gout and hyperuricemia and related conditions.

In one embodiment of its compound aspect, this invention provides or utilizes compounds of Formula IA:

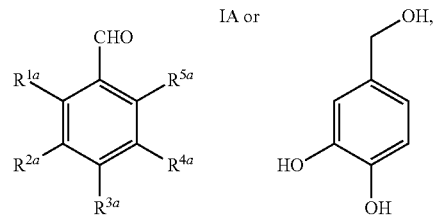

or a tautomer, and/or a pharmaceutically acceptable salt and/or solvate thereof;
wherein $R^{1a}$, $R^{2a}$, $R^{3a}$, $R^{4a}$, and $R^{5a}$ are each independently selected from hydrogen, hydroxyl, nitro, cyano, fluoro, chloro, bromo, trifluoromethyl, sulfonyl, and aldehyde, and wherein $R^{1a}$, $R^{2a}$, $R^{3a}$, $R^{4a}$, and $R^{5a}$ are not simultaneously hydrogen.

In one embodiment the compounds of Formula IA are:

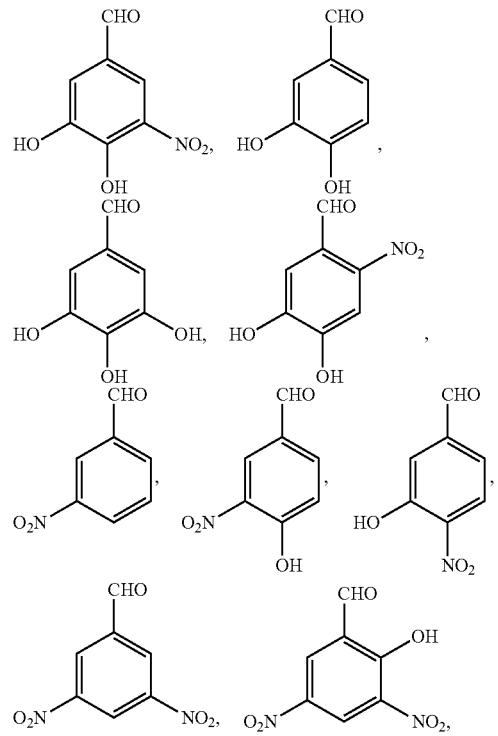

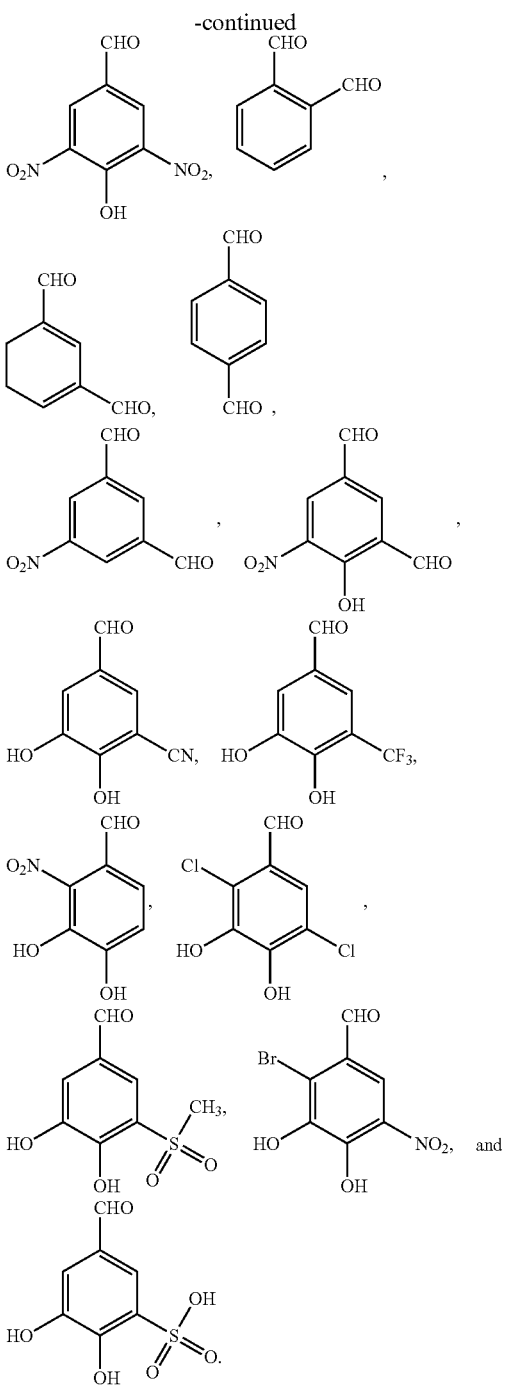

In another embodiment, the compounds provided or utilized herein are xanthine oxidase inhibitors which include compounds of Formula I:

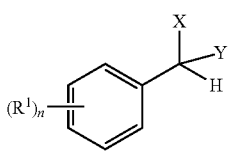

I wherein;
n is an integer of from 1 to 5;
X and Y are independently selected from the group consisting of —$OR^3$, —$SR^3$, —$NHR^3$, and —$NHOR^3$ or X and Y are joined together to form =O, =S, =$NR^3$, =$NOR^3$ or a cyclic ring system of the formula

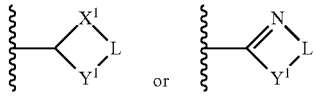

where $X^1$ and $Y^1$ are independently selected from the group consisting of —O—, —S—, —$SO_2$—, and —N($R^3$)—, and L is —C(O)— or $C_2$ to $C_4$ alkylene group optionally substituted with one or two oxo;
each $R^3$ is selected from the group consisting of hydrogen and $C_1$ to $C_4$ alkyl;
each $R^1$ is independently selected from the group consisting of:
halogen, hydroxy, nitro, nitroso, cyano, aldehyde, $C_1$ to $C_6$ alkyl, —$CH_2OH$, halogenated $C_1$ to $C_4$ alkyl, phenyl, —$SO_2H$,
—$OR^4$, —OC(=O)$R^4$, —OC(=O)NH$R^4$, —OC(=S)$R^4$, —OC(=S)NH$R^4$, —OC(=O)O$R^4$, —OC(=O)S$R^4$, —OC(=S)O$R^4$,
—OP(=O)$R^4$, —OP(=O)$_2R^4$, —OP(=O)NH$R^4$, —OP(=O)$_2$NH$R^4$, —OP(=S)NH$R^4$, —OP(=O)O$R^4$, —OP(=O)$_2$O$R^4$, —OP(=O)S$R^4$, —OP(=O)$_2$S$R^4$, —OP(=S)O$R^4$,
—OS(=O)$R^4$, —OS(=O)$_2R^4$, —OS(=O)NH$R^4$, —OS(=O)$_2$NH$R^4$, —OS(=O)O$R^4$, and —OS(=O)$_2$O$R^4$;
or two of $R^1$ groups are joined together to form a 5 or 6-membered heterocyclic ring having 1 to 3 heteroatoms selected from O, Si$R^4$, S, SO, $SO_2$, N, P(=S), P(=O), P(=O)$_2$, and N$R^{10}$, wherein the heterocyclic ring is optionally substituted by $R^5$;
or one of $R^1$ and one of Y or X are joined together to form a 5 or 6-membered heterocyclic ring having 1 to 3 heteroatoms selected from O, Si$R^4$, S, $SO_2$, N, P, P(O), P(O)$_2$, and N$R^{10}$, wherein the heterocyclic ring is optionally substituted by $R^5$;
$R^4$ is selected from the group consisting of hydrogen, $C_1$-$C_6$ alkyl, $C_1$-$C_6$ alkoxy, $C_3$-$C_7$ cycloalkyl, $C_2$-$C_6$ alkenyl, $C_4$-$C_7$ cycloalkenyl, $C_2$-$C_6$ alkynyl, $C_6$-$C_{10}$ aryl, and $C_5$-$C_6$ heteoaryl or heterocycle having 1 to 3 heteroatoms selected from O, S, $SO_2$, N, $NR^{11}$ and $R^{30}$;
or —$OR^4$ is a hydroxy group esterified with a phospholipid;
$R^5$ is selected from the group consisting of $C_1$-$C_6$ alkyl, $C_1$-$C_6$ alkoxy, $C_3$-$C_7$ cycloalkyl, $C_2$-$C_6$ alkenyl, $C_4$-$C_7$ cycloalkenyl, $C_2$-$C_6$ alkynyl, $C_6$-$C_{10}$ aryl, and $C_5$-$C_6$ heteoaryl or heterocycle having 1 to 3 heteroatoms selected from O, S, $SO_2$, N, and $NR^{11}$; or two $R^5$ on a same carbon form =O or =S;
$R^{10}$ is hydrogen or $C_1$ to $C_6$ alkyl or $C_3$ to $C_7$ cycloalkyl ring optionally substituted by $R^5$;
$R^{11}$ is hydrogen or $C_1$ to $C_6$ alkyl, or $C_5$-$C_6$ heteroaryl having 1 to 3 heteroatoms selected from O, S, $SO_2$, N, and $NR^{12}$;
$R^{12}$ is hydrogen or $C_1$ to $C_6$ alkyl; and
$R^{30}$ is a saturated fatty chain or an unsaturated fatty chain, or a tautomer, and/or a pharmaceutically acceptable salt and/or solvate thereof.

Preferably, the saturated fatty chain or the unsaturated fatty chain contains 10-30 chain carbons, or more preferably, 12-18 chain carbons. In some embodiments, the saturated fatty chain or the unsaturated fatty chain contains less than 10 chain carbons. As used herein, a fatty chain refers to a hydrocarbyl chain. In some embodiments, the unsaturated fatty chain contains up to 4, preferably, up to 2, more preferably, a single carbon carbon double bond within the fatty chain.

In one embodiment, there is provided or utilized a compound of formula II:

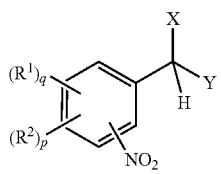

II or a tautomer, a pharmaceutically acceptable salt and/or solvate thereof,
wherein
$R^1$ is as defined above in Formula I and q is 1, 2 or 3;
$R^2$ is selected from halo, nitro, aldehyde and hydroxyl and p is 1, 2 or 3, provided that p+q is no more than 4; and
X and Y are as defined above.

In one embodiment, there is provided a compound of formula III:

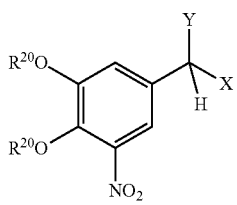

III or a tautomer, a pharmaceutically acceptable salt and/or solvate thereof,
where X and Y are as defined above in Formula I and each $R^{20}$ is independently selected from the group consisting of hydrogen, —C(=O)$R^4$, —C(=O)NH$R^4$, —C(=S)$R^4$, —C(=S)NH$R^4$, —C(=O)O$R^4$, —C(=O)S$R^4$, —C(=S)O$R^4$,
—P(=O)$R^4$, —P(=O)$_2R^4$, —P(=O)NH$R^4$, —P(=O)$_2$NH$R^4$, —P(=S)NH$R^4$, —P(=O)O$R^4$, —P(=O)$_2$O$R^4$, —P(=O)S$R^4$, —P(=O)$_2$S$R^4$, and —P(=S)O$R^4$, wherein $R^4$ is as defined above in Formula I.

In another embodiment, there is provided or utilized a compound of formula IV as provided in the table below:

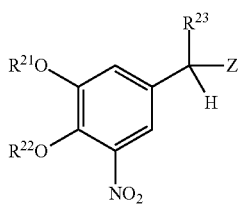

IV

| Compound No. | $R^{21}$ | $R^{22}$ | $R^{23}$ | Z |
|---|---|---|---|---|
| 1 | —CH$_3$ | —CH$_3$ | —OCH$_3$ | —OCH$_3$ |
| 2 | —CH$_3$ | —CH$_3$ | —OCH$_2$CH$_3$ | —OCH$_2$CH$_3$ |
| 3 | —CH$_2$CH$_3$ | —CH$_2$CH$_3$ | —OCH$_2$CH$_3$ | —OCH$_2$CH$_3$ |
| 4 | —CH$_3$ | —CH$_3$ | —SCH$_3$ | —SCH$_3$ |
| 5 | —CH$_3$ | —CH$_3$ | —SCH$_2$CH$_3$ | —SCH$_2$CH$_3$ |
| 6 | —CH$_3$ | —CH$_3$ | —OCH$_3$ | —OCH$_3$ |
| 7 | —CH$_3$ | —CH$_3$ | —OCH$_3$ | —OCH$_3$ |
| 8 | —CH$_3$ | —CH$_3$ | —OCH$_3$ | —OCH$_3$ |
| 9 | —CH$_2$CH$_3$ | —C(O)CH$_2$CH$_3$ | —OCH$_2$CH$_3$ | —OCH$_2$CH$_3$ |
| 10 | —SO$_3$H | —SO$_3$H | —OCH$_3$ | —OCH$_3$ |
| 11 | —PO$_3$H | —PO$_3$H | —OCH$_3$ | —OCH$_3$ |
| 12 | —COCF$_3$ | —COCF$_3$ | —OCF$_3$ | —OCF$_3$ |
| 13 | —CH$_2$CH$_3$ | —CH$_2$CH$_3$ | —NHOH | —OCH$_3$ |
| 14 | —CH$_3$ | —CH$_3$ | —OCH$_3$ | —OCH$_3$ |
| 15 | —CH$_3$ | —CH$_3$ | —OCH$_3$ | —OCH$_3$ |
| 16 | —CH$_3$ | —CH$_3$ | —NHCH$_3$ | —NH |
| 17 | —PO$_3$H | —PO$_3$H |  | =O |
| 18 | —C(O)CH$_3$ | —C(O)CH$_3$ |  | =O | or a tautomer, and/or a pharmaceutically acceptable salt and/or solvate thereof

In another embodiment, provided or utilized are compounds selected from the group consisting of:

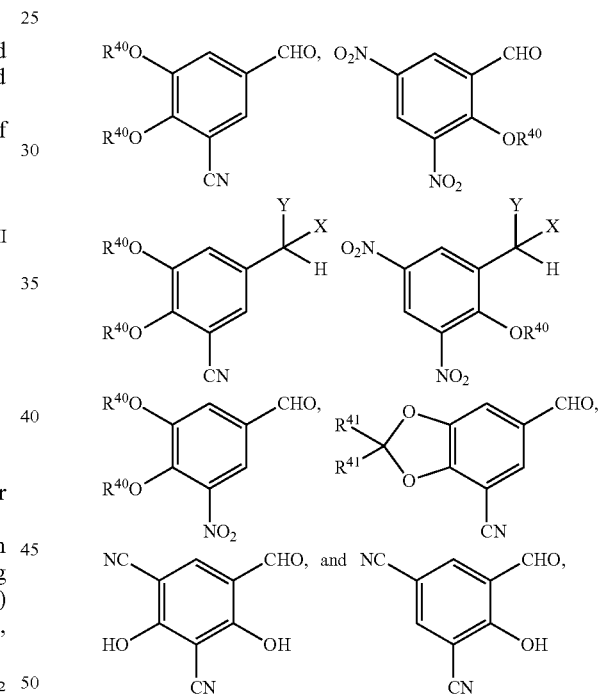

where $R^{40}$ is hydrogen, $R^{30}$ or —COR$^{30}$, each $R^{41}$ independently is saturated or unsaturated fatty chain, such as $R^{30}$, or is hydrogen, and where X and Y are defined as in any aspect and embodiment above, and are preferably independently selected from the group consisting of —OR$^3$, —SR$^3$, —NHR$^3$, and —NHOR$^3$ or X and Y are joined together to form =O, =S, =NR$^3$, =NOR$^3$ or a cyclic ring system of the formula

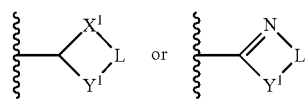

where $X^1$ and $Y^1$ are independently selected from the group consisting of —O—, —S—, —SO$_2$—, and —N(R$^3$)—, and L is —C(O)— or C$_2$ to C$_4$ alkylene group optionally substituted with one or two oxo, or a tautomer, and/or a pharmaceutically acceptable salt and/or solvate thereof.

Preferably, the saturated fatty chain or the unsaturated fatty chain contains 10-30 chain carbons, or more preferably, 12-18 chain carbons. In some embodiments, the saturated fatty chain or the unsaturated fatty chain contains less than 10 chain carbons. As used herein, a fatty chain refers to a hydrocarbyl chain.

In preferred embodiments, the hydroxy groups, preferably, one or two hydroxy groups, present in the compounds described herein can be esterified with a saturated fatty acid or an unsaturated fatty acid, or a phospholipid.

In a particular embodiment, the compound of Formula I is not a compound of Formula IA or a tautomer, a pharmaceutically acceptable salt and/or solvate thereof.

In another particularly preferred embodiment, the compound of Formula I is not a compound described in U.S. patent application Ser. No. 13/790,083, filed Mar. 8, 2013, which is herein incorporated by reference in its entirety.

In one embodiment, this invention is directed to a pharmaceutical composition comprising a pharmaceutically acceptable excipient and a compound of Formula IA, I, II, II, or IV above or a tautomer, solvate and/or a pharmaceutically acceptable salt thereof.

In one embodiment the compound utilized herein is 3,4-dihydroxy-5-cyanobenzaldehyde (DHCB) or 3,5-dinitrosalicylaldehyde (DNSA).

In one embodiment of its method aspect, there is a provided a method for treating a condition mediated at least in part by xanthine oxidase which method comprises administering to a patient suffering from such a condition a therapeutically effective amount of a compound of any of Formulae IA, I, II, III and IV above or a tautomer or a pharmaceutically acceptable salt and/or solvate thereof, or a therapeutically effective amount of DHCB or DNSA.

In one embodiment of its method aspect, there is a provided a method for reducing uric acid and/or reactive oxygen species production in a patient in need thereof, which method comprises administering to the patient an effective amount of a compound of any of Formula IA, I, II, III and IV above or a tautomer or a pharmaceutically acceptable salt and/or solvate thereof, or a therapeutically effective amount of DHCB or DNSA.

In one of its embodiments, this invention is directed to a method for treating, for example, gout, hypoxia, or hyperuricemia in a patient which method comprises administering to the patient in need thereof a therapeutically effective amount of a compound of any of Formulae IA, I, II, III and IV above or a tautomer or a pharmaceutically acceptable salt and/or solvate thereof.

DETAILED DESCRIPTION

Figure 1A:
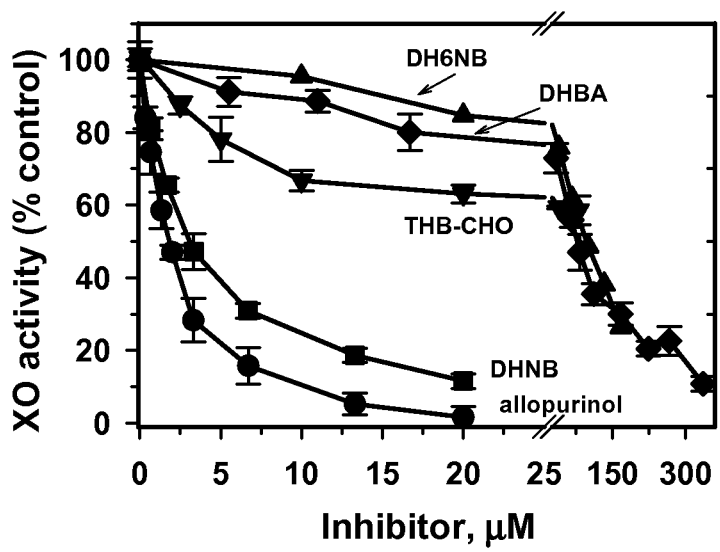
FIG. 1A is a graph showing the inhibition of xanthine oxidase (XO) activity by test compounds (DH6NB, DHBA, THB-CHO, and DHNB) and a control compound (allopurinol).

Provided herein are derivatives of small molecule xanthine oxidase inhibitors and methods for their use in treating conditions mediated, at least in part, by xanthine oxidase in a patient. The xanthine oxidase inhibitors are administered in an effective amount to treat, for example, gout, hypoxia, or hyperuricemia in a subject.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Throughout this application, various publications are referenced. The disclosures of these publications in their entireties are hereby incorporated by reference into this application.

Definitions

As used herein, the following definitions shall apply unless otherwise indicated. Further, if any term or symbol used herein is not defined as set forth below, it shall have its ordinary meaning in the art.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—, or Me), ethyl ($CH_3CH_2$—, or Et), n-propyl ($CH_3CH_2CH_2$—, or n-Pr), isopropyl (($CH_3)_2CH$—, or i-Pr), n-butyl ($CH_3CH_2CH_2CH_2$—, or n-Bu), isobutyl (($CH_3)_2CHCH_2$—, or i-Bu), sec-butyl (($CH_3)(CH_3CH_2)CH$—, or s-Bu), t-butyl (($CH_3)_3C$—, or t-Bu), n-pentyl ($CH_3CH_2CH_2CH_2CH_2$—), and neopentyl (($CH_3)_3CCH_2$—). $C_x$ alkyl refers to an alkyl group having x number of carbon atoms.

"Alkylene" refers to a divalent alkyl group, such as —$CH_2$—, —$CH_2CH_2$—, —$CH_2CH_2CH_2$—, —$CH(CH_3)CH_2$—, etc.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH). $C_x$ alkynyl refers to an alkynyl group having x number of carbon atoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" or "Ar" refers to a monovalent aromatic carbocyclic group of from 6 to 10 carbon atoms having a single ring (e.g., phenyl (Ph)) or multiple condensed rings (e.g., naphthyl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Heterocycle" or "heterocyclic" refers to a saturated or partially saturated, but not aromatic, group having from 1 to 10 ring carbon atoms and from 1 to 4 ring heteroatoms selected from the group consisting of nitrogen, phosphorus, sulfur, or oxygen. $C_x$ cycloalkyl refers to a heterocycle group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen, phosphorus and/or sulfur atom(s) of the heterocyclic group are optionally oxidized to provide for the N-oxide, P(O), P(O)$_2$, P(O)$_3$, sulfinyl, or sulfonyl moieties.

"Aldehyde" refers to the group —CHO.

"Nitro" refers to the group —$NO_2$.

"Nitroso" refers to the group —N=O.

"Oxo" refers to the atom (=O) or (—O$^-$).

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs of the disease in a subject as compared to a control. As used herein, control refers to the untreated condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means primarily mammals. Mammals include, for example, humans; non-human primates, e.g., apes and monkeys; cattle; horses; sheep; rats; mice; pigs; and goats.

As used herein, the term "condition" or "disorder" refers to a state of a patient (or an organ or tissue of the patient) that deviates from the normal state and may at least cause discomfort, such as pain or abnormal appearance, such as redness in color, or can lead to a condition which may cause discomfort such that treatment is desired.

It is understood that the above definitions are not intended to include impermissible substitution patterns (e.g., methyl substituted with 5 fluoro groups). Such impermissible substitution patterns are well known to the skilled artisan.

Compounds

In one embodiment of its compound aspect, this invention provides compounds of Formula IA:

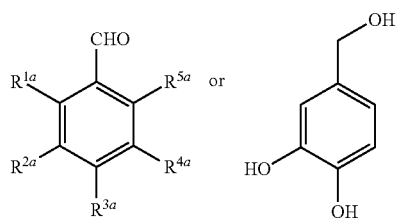

and tautomer, solvates and/or pharmaceutically acceptable salts thereof;
wherein $R^{1a}$, $R^{2a}$, $R^{3a}$, $R^{4a}$, and $R^{5a}$ are each independently selected from hydrogen, hydroxyl, nitro, cyano, fluoro, chloro, bromo, trifluoromethyl, sulfonyl, and aldehyde, wherein $R^{1a}$, $R^{2a}$, $R^{3a}$, $R^{4a}$, and $R^{5a}$ are not simultaneously hydrogen.

In one embodiment of Formula IA, the sulfonyl is methylsulfonyl or sulfonic acid.

In one embodiment the compounds of Formula IA are:

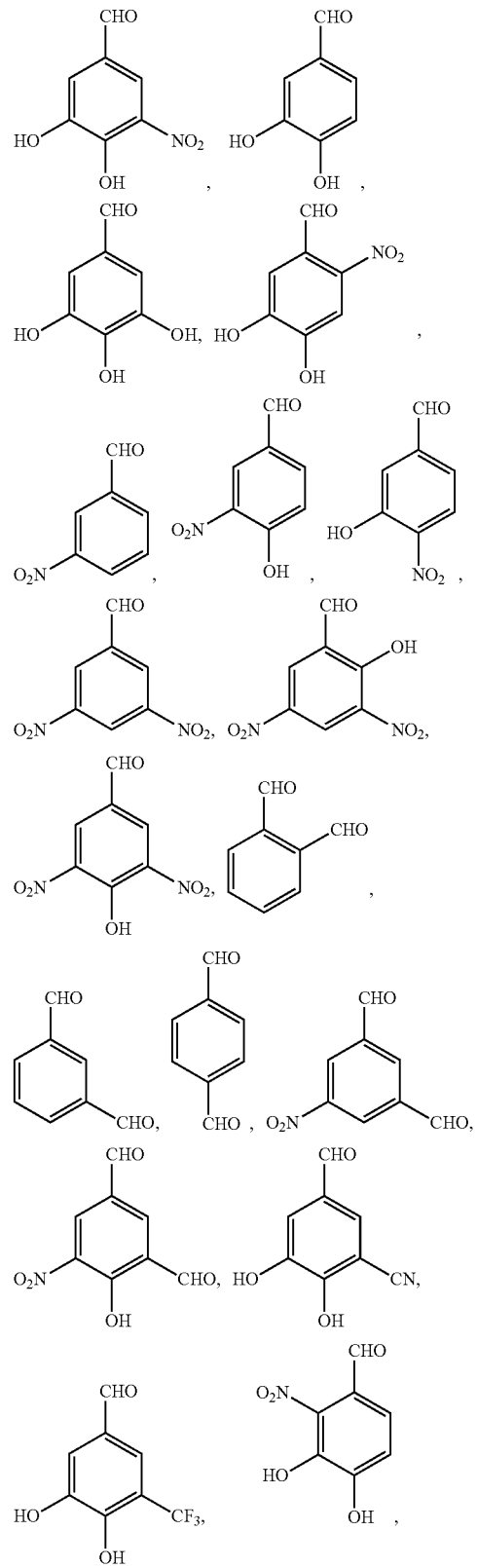

-continued

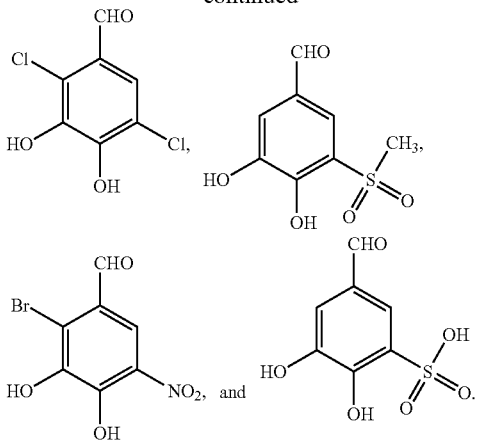

In another embodiment, the compounds disclosed herein are xanthine oxidase inhibitors which include compounds of Formula I:

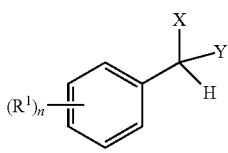

I wherein;

n is an integer of from 1 to 5;

X and Y are independently selected from the group consisting of —$OR^3$, —$SR^3$, —$NHR^3$, and —$NHOR^3$ or X and Y are joined together to form =O, =S, =$NR^3$, =$NOR^3$ or a cyclic ring system of the formula

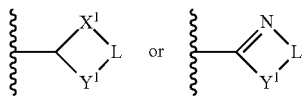

where $X^1$ and $Y^1$ are independently selected from the group consisting of —O—, —S—, —$SO_2$—, and —N($R^3$)—, and L is —C(O)— or $C_2$ to $C_4$ alkylene group optionally substituted with one or two oxo;

each $R^3$ is selected from the group consisting of hydrogen and $C_1$ to $C_4$ alkyl;

each $R^1$ is independently selected from the group consisting of:
halogen, hydroxy, nitro, nitroso, cyano, aldehyde, $C_1$ to $C_6$ alkyl, —$CH_2OH$, halogenated $C_1$ to $C_4$ alkyl, phenyl, —$SO_2H$,
—$OR^4$, —OC(=O)$R^4$, —OC(=O)NH$R^4$, —OC(=S)$R^4$, —OC(=S)NH$R^4$, —OC(=O)O$R^4$, —OC(=O)S$R^4$, —OC(=S)O$R^4$,
—OP(=O)$R^4$, —OP(=O)$_2R^4$, —OP(=O)NH$R^4$, —OP(=O)$_2$NH$R^4$, —OP(=S)NH$R^4$, —OP(=O)O$R^4$, —OP(=O)$_2$O$R^4$, —OP(=O)S$R^4$, —OP(=O)$_2$S$R^4$, —OP(=S)O$R^4$,
—OS(=O)$R^4$, —OS(=O)$_2R^4$, —OS(=O)NH$R^4$, —OS(=O)$_2$NH$R^4$, —OS(=O)O$R^4$, and —OS(=O)$_2$O$R^4$;

or two of $R^1$ groups are joined together to form a 5 or 6-membered heterocyclic ring having 1 to 3 heteroatoms selected from O, Si$R^4$, S, SO, $SO_2$, N, P(=S), P(=O), P(=O)$_2$, and N$R^{10}$, wherein the heterocyclic ring is optionally substituted by $R^5$;

or one of $R^1$ and one of Y or X are joined together to form a 5 or 6-membered heterocyclic ring having 1 to 3 heteroatoms selected from O, Si$R^4$, S, $SO_2$, N, P, P(O), P(O)$_2$, and N$R^{10}$, wherein the heterocyclic ring is optionally substituted by $R^5$;

$R^4$ is selected from the group consisting of hydrogen, $C_1$-$C_6$ alkyl, $C_1$-$C_6$ alkoxy, $C_3$-$C_7$ cycloalkyl, $C_2$-$C_6$ alkenyl, $C_4$-$C_7$ cycloalkenyl, $C_2$-$C_6$ alkynyl, $C_6$-$C_{10}$ aryl, and $C_5$-$C_6$ heteoaryl or heterocycle having 1 to 3 heteroatoms selected from O, S, $SO_2$, N, and N$R^{11}$;

$R^5$ is selected from the group consisting of $C_1$-$C_6$ alkyl, $C_1$-$C_6$ alkoxy, $C_3$-$C_7$ cycloalkyl, $C_2$-$C_6$ alkenyl, $C_4$-$C_7$ cycloalkenyl, $C_2$-$C_6$ alkynyl, $C_6$-$C_{10}$ aryl, and $C_5$-$C_6$ heteoaryl or heterocycle having 1 to 3 heteroatoms selected from O, S, $SO_2$, N, and N$R^{11}$; or two $R^5$ on a same carbon form =O or =S;

$R^{10}$ is hydrogen or $C_1$ to $C_6$ alkyl or $C_3$ to $C_7$ cycloalkyl ring optionally substituted by $R^5$;

$R^{11}$ is hydrogen or $C_1$ to $C_6$ alkyl, or $C_5$-$C_6$ heteroaryl having 1 to 3 heteroatoms selected from O, S, $SO_2$, N, and N$R^{12}$; and $R^{12}$ is hydrogen or $C_1$ to $C_6$ alkyl;

or a tautomer, solvate and/or a pharmaceutically acceptable salt thereof.

In one embodiment, there is provided a compound of formula II:

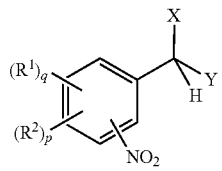

II or a tautomer, a pharmaceutically acceptable salt and/or solvate thereof, wherein $R^1$ is as defined above in Formula I and q is 1, 2 or 3;

$R^2$ is selected from halo, nitro, aldehyde and hydroxyl and p is 0, 1, 2 or 3, provided that p+q is no more than 4; and X and Y are as defined above.

In some embodiments, $R^1$ is selected from the group consisting of —OC(=O)$R^4$, —OC(=O)NH$R^4$, —OC(=S)$R^4$, —OC(=S)NH$R^4$, —OC(=O)O$R^4$, —OC(=O)S$R^4$, and —OC(=S)O$R^4$.

In some embodiments, $R^1$ is selected from the group consisting of —OP(=O)$R^4$, —OP(=O)$_2R^4$, —OP(=O)NH$R^4$, —OP(=O)$_2$NH$R^4$, —OP(=S)NH$R^4$, —OP(=O)O$R^4$, —OP(=O)$_2$O$R^4$, —OP(=O)S$R^4$, —OP(=O)$_2$S$R^4$, and —OP(=S)O$R^4$.

In some embodiments, $R^1$ is selected from the group consisting of —OS(=O)$R^4$, —OS(=O)$_2R^4$, —OS(=O)NH$R^4$, —OS(=O)$_2$NH$R^4$, —OS(=O)O$R^4$, and —OS(=O)$_2$O$R^4$.

In one embodiment, there is provided a compound of formula III:

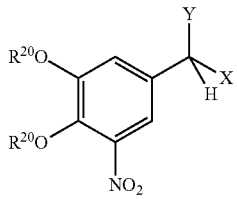

or a tautomer, a pharmaceutically acceptable salt and/or solvate thereof, where X and Y are as defined above in Formula I and each $R^{20}$ is independently selected from the group consisting of hydrogen, —C(=O)$R^4$, —C(=O)NH$R^4$, —C(=S)$R^4$, —C(=S)NH$R^4$, —C(=O)O$R^4$, —C(=O)S$R^4$, —C(=S)O$R^4$, —P(=O)$R^4$, —P(=O)$_2R^4$, —P(=O)NH$R^4$, —P(=O)$_2$NH$R^4$, —P(=S)NH$R^4$, —P(=O)O$R^4$, —P(=O)$_2$O$R^4$, —P(=O)S$R^4$, —P(=O)$_2$S$R^4$, and —P(=S)O$R^4$, wherein $R^4$ is as defined above in Formula I.

In some embodiments, X and Y are independently selected from the group consisting of —O$R^3$, —S$R^3$, —NH$R^3$, and —NHO$R^3$. In some embodiments, X and Y are both —O$R^3$, wherein $R^3$ is $C_1$ to $C_4$ alkyl. In some embodiments, X and Y are both —NH$R^3$, wherein $R^3$ is $C_1$ to $C_4$ alkyl. In some embodiments, X and Y are both —S$R^3$, wherein $R^3$ is $C_1$ to $C_4$ alkyl. In some embodiments, $R^1$ is independently selected from the group consisting of halogen, hydroxy, nitro, nitroso, cyano, and aldehyde.

In some embodiments, X and Y are joined together to form =O, =S, =N$R^3$, or =NO$R^3$. In some embodiments, at least one of $R^1$ is selected from the group consisting of —OC(=O)$R^4$, —OC(=O)NH$R^4$, —OC(=S)$R^4$, —OC(=S)NH$R^4$, —OC(=O)O$R^4$, —OC(=O)S$R^4$, —OC(=S)O$R^4$, —OP(=O)$R^4$, —OP(=O)$_2R^4$, —OP(=O)NH$R^4$, —OP(=O)$_2$NH$R^4$, —OP(=S)NH$R^4$, —OP(=O)O$R^4$, —OP(=O)$_2$O$R^4$, —OP(=O)S$R^4$, —OP(=O)$_2$S$R^4$, —OP(=S)O$R^4$, —OS(=O)$R^4$, —OS(=O)$_2R^4$, —OS(=O)NH$R^4$, —OS(=O)$_2$NH$R^4$, —OS(=O)O$R^4$, and —OS(=O)$_2$O$R^4$.

In some embodiments, X and Y are joined together to form a cyclic ring system of the formula

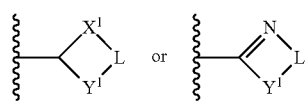

wherein $X^1$, $Y^1$ and L are as defined above in Formula I.

In some embodiments, L is —C(O)—. In some embodiments, L is $C_2$ to $C_4$ alkylene group. In some embodiments, L is $C_2$ to $C_4$ alkylene group substituted with one oxo. In some embodiments, L is $C_3$ to $C_4$ alkylene group substituted with two oxo. In some embodiments, L is —C(O)CH$_2$—. In some embodiments, L is —C(O)CH$_2$CH$_2$—.

In some embodiments, X and Y are joined together to form a cyclic ring system selected from:

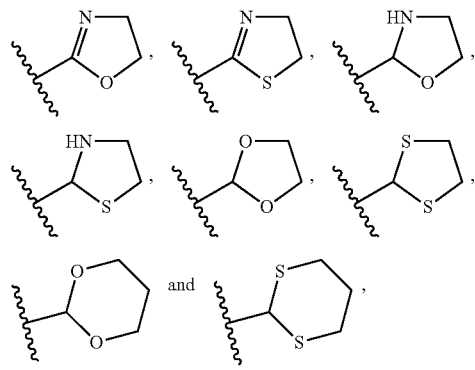

In some embodiments, $R^1$ is independently selected from the group consisting of halogen, hydroxy, nitro, nitroso, cyano, and aldehyde.

In another embodiment, there is provided a compound of formula IV as provided in the table below:

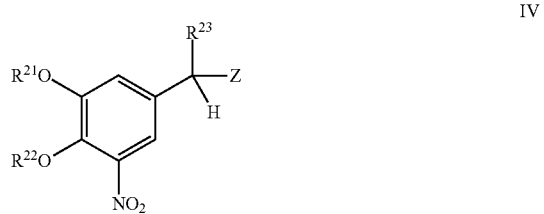

| Compound No. | $R^{21}$ | $R^{22}$ | $R^{23}$ | Z |
|---|---|---|---|---|
| 1 | —CH$_3$ | —CH$_3$ | —OCH$_3$ | —OCH$_3$ |
| 2 | —CH$_3$ | —CH$_3$ | —OCH$_2$CH$_3$ | —OCH$_2$CH$_3$ |
| 3 | —CH$_2$CH$_3$ | —CH$_2$CH$_3$ | —OCH$_2$CH$_3$ | —OCH$_2$CH$_3$ |
| 4 | —CH$_3$ | —CH$_3$ | —SCH$_3$ | —SCH$_3$ |
| 5 | —CH$_3$ | —CH$_3$ | —SCH$_2$CH$_3$ | —SCH$_2$CH$_3$ |
| 6 | —CH$_3$ | —CH$_3$ | —OCH$_3$ | —OCH$_3$ |
| 7 | —CH$_3$ | —CH$_3$ | —OCH$_3$ | —OCH$_3$ |
| 8 | —CH$_3$ | —CH$_3$ | —OCH$_3$ | —OCH$_3$ |
| 9 | —CH$_2$CH$_3$ | —C(O)CH$_2$CH$_3$ | —OCH$_2$CH$_3$ | —OCH$_2$CH$_3$ |
| 10 | —SO$_3$H | —SO$_3$H | —OCH$_3$ | —OCH$_3$ |
| 11 | —PO$_3$H | —PO$_3$H | —OCH$_3$ | —OCH$_3$ |
| 12 | —COCF$_3$ | —COCF$_3$ | —OCF$_3$ | —OCF$_3$ |
| 13 | —CH$_2$CH$_3$ | —CH$_2$CH$_3$ | —NHOH | —OCH$_3$ |
| 14 | —CH$_3$ | —CH$_3$ | —OCH$_3$ | —OCH$_3$ |
| 15 | —CH$_3$ | —CH$_3$ | —OCH$_3$ | —OCH$_3$ |
| 16 | —CH$_3$ | —CH$_3$ | —NHCH$_3$ | —NH |
| 17 | —PO$_3$H | —PO$_3$H |  | =O |
| 18 | —C(O)CH$_3$ | —C(O)CH$_3$ |  | =O | or a tautomer, and/or a pharmaceutically acceptable salt and/or solvate thereof

In another embodiment, there is provided a compound selected from:

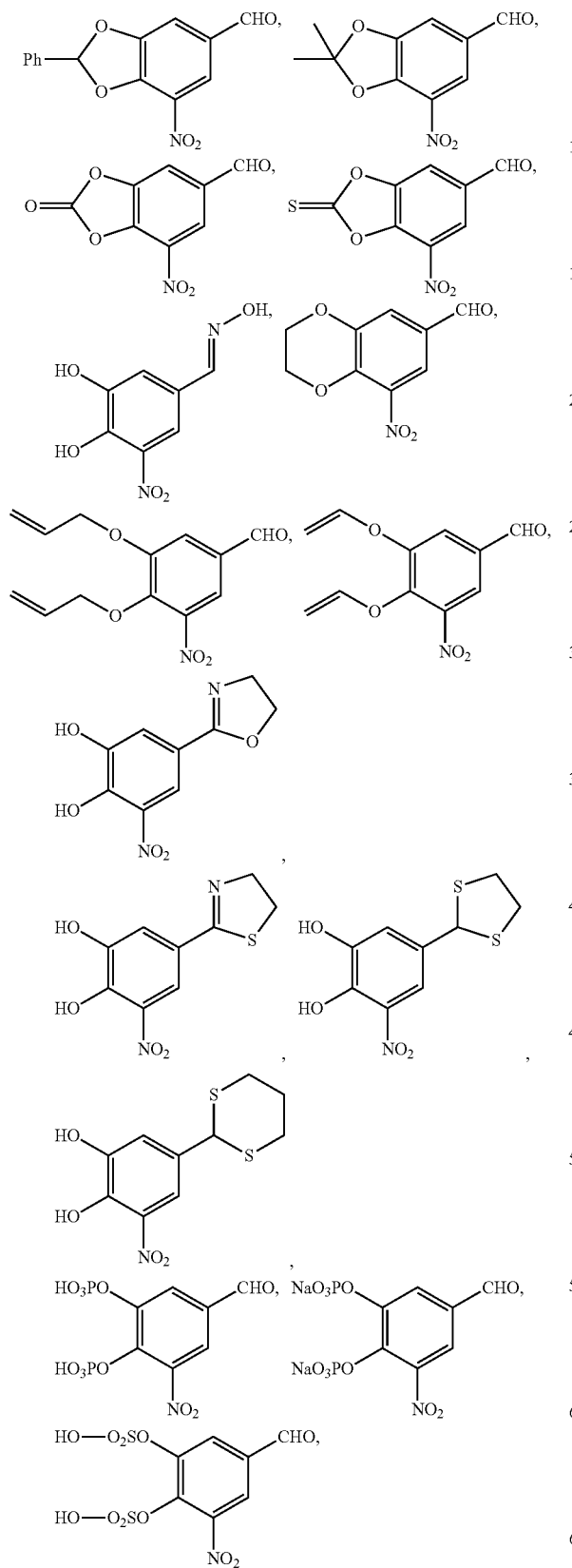

or a tautomer, and/or a pharmaceutically acceptable salt and/or solvate thereof

In still another embodiment, there is provide a compound selected from:
7-nitro-2-phenylbenzo[d][1,3]dioxole-5-carbaldehyde;
5-(1,3-dioxolan-2-yl)-3-nitrobenzene-1,2-diol;
6-(1,3-dioxolan-2-yl)-4-nitrobenzo[d][1,3]dioxole;
(7-nitro-2-oxobenzo[d][1,3]dioxol-5-yl)methylene diacetate,
3,4-bis(allyloxy)-5-nitrobenzaldehyde;
and 7-nitro-2-oxobenzo[d][1,3]dioxole-5-carbaldehyde;
or a tautomer, and/or a pharmaceutically acceptable salt and/or solvate thereof In a particular embodiment, the compound of Formula I is not a compound of Formula IA or a tautomer, a pharmaceutically acceptable salt and/or solvate thereof In another particular embodiment, the compound of Formula I is not a compound selected from:

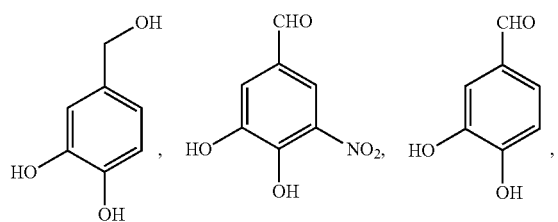

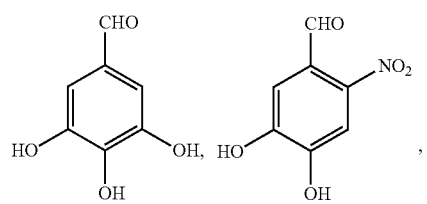

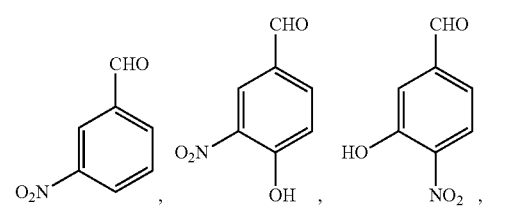

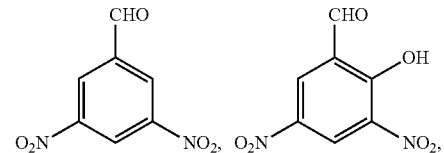

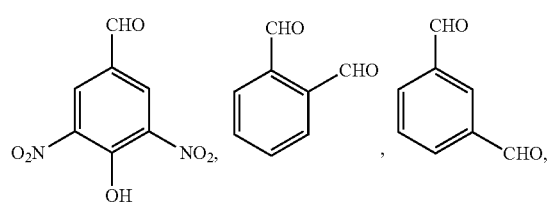

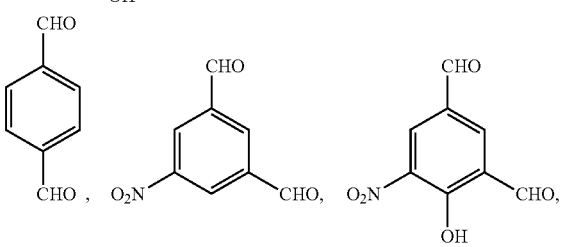

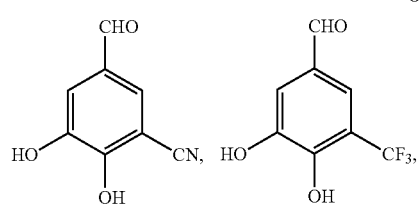

-continued

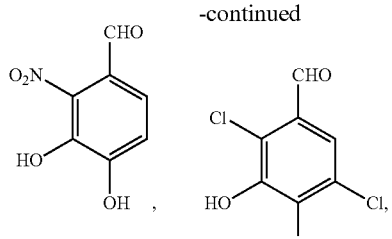

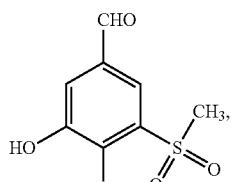

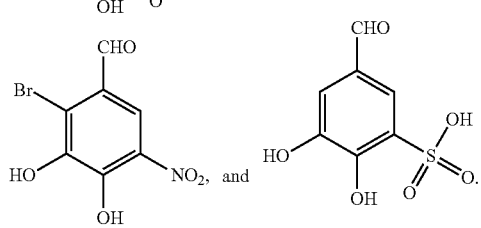

or a tautomer, a pharmaceutically acceptable salt and/or solvate thereof

In one aspect, the compounds are effective at improving the bioavailability of any such compound resulting from metabolism as xanthine inhibitors. These compounds are particularly useful as anti-gout, anti-hypoxia, and anti-hyperuricemia drugs. The solubility and/or bioavailabilty, controlled for example by absorption thru a tissue membrane, may be substantially increased by administration of the appropriate compound as described herein. Advantageously, these compounds exhibit significantly enhanced pharmacokinetic properties in comparison to other xanthine inhibitors. These improvements result in more of the drug being absorbed and reaching the target; thus, pill burden, overall cost of the therapy, and dosing intervals are be reduced.

Pharmaceutical Formulations

The compounds described herein and derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compounds described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein).

A solvate of a compound is a solid-form of the compound that crystallizes with less than one, one or more than one molecules of solvent inside in the crystal lattice. A few examples of solvents that can be used to create solvates, such as pharmaceutically acceptable solvates, include, but are not limited to, water, C1-C6 alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The drug can be administered at a suitable schedule such as once a day, twice a day, three times a day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Although compositions suitable for oral, intravenous or intraarterial delivery will probably be used most frequently, other routes that may be used include peroral, pulmonary, rectal, nasal, vaginal, lingual, intramuscular, intraperitoneal, intracutaneous, transdermal and subcutaneous routes. The choice of formulation depends on various factors such as the mode of drug administration and bioavailability of the drug substance.

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors well known to the skilled artisan.

The amount of the compound in a formulation can vary within the full range employed by those skilled in the art. Typically, the formulation will contain, on a weight percent (wt %) basis, from about 0.01 to 99.99 wt % of a compound of this invention based on the total formulation, with the balance being one or more suitable pharmaceutical excipients. In some embodiments, the compound is present at a level of about 1 to 80 wt %. In a liquid composition, a compound of this invention should generally be present in such compositions at a concentration of between about 0.1 and 20 mg/ml.

FORMULATION EXAMPLES

The following are representative pharmaceutical formulations containing a compound of Formula IA, I, II, III, or IV.

Formulation Example 1

Tablet formulation

The following ingredients are mixed intimately and pressed into single scored tablets.

| Ingredient | tablet, mg |
|---|---|
| compound of this invention | 400 |
| cornstarch | 50 |
| croscarmellose sodium | 25 |
| lactose | 120 |
| magnesium stearate | 5 |

Formulation Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Formulation Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4

Injectable Formulation

The following ingredients are mixed to form an injectable formulation.

| Ingredient | Amount |
|---|---|
| compound of this invention | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
|---|---|
| Compound of the invention | 500 mg |
| Witepsol ® H-15 | balance |

Methods of Use

Also provided herein are methods for treating a disorder mediated, at least in part, by xanthine oxidase. Examples of such disorders include, but are not limited to: gout, hypoxia, or hyperuricemia in a subject.

A method of treating gout, hypoxia, or hyperuricemia in a subject includes administering to the subject an effective amount of a xanthine oxidase inhibitor as described herein. Optionally, the methods for treating gout, hypoxia, or hyperuricemia in a subject can further include administering a second therapeutic agent, such as an anti-gout agent (e.g., allopurinol, benzbromarone, colchicine, probenecid, or sulfinpyrazone), an anti-inflammatory agent, or an antioxidant, to the subject. Optionally, the compound may be administered orally to the subject.

Further provided herein are methods for reducing uric acid production and/or reactive oxygen species production in a subject. The methods include administering to the subject an effective amount of a xanthine oxidase inhibitor as described herein.

Optionally, the methods for reducing uric acid production and/or reactive oxygen species production further comprise selecting a subject having gout, hypoxia, or hyperuricemia.

Methods of inhibiting xanthine oxidase activity in a cell are also provided herein. The methods include contacting a cell with an effective amount of a xanthine oxidase inhibitor as described herein. Optionally, the contacting is performed in vivo. Optionally, the contacting is performed in vitro.

The compounds represented by Formula IA, I, II, III, or IV or their tautomers, solvates and/or pharmaceutically acceptable salts thereof can effectively act as inhibitors of xanthine oxidase and reduce uric acid and/or reactive oxygen species production. In one aspect of this invention, the invention provides a method for inhibiting xanthine oxidase and/or a method for treating a condition, mediated at least in part by xanthine oxidase, for example, gout, hypoxia, or hyperuricemia, with an effective amount of one or more compound of Formula IA, I, II, III, or IV or their tautomers, solvates and/or pharmaceutically acceptable salts as provided herein.

In one of its method aspects, this invention is directed to a method for inhibiting xanthine oxidase in a cell which method comprises contacting the cell with an effective amount of one or more compound of Formula IA, I, II, III, or IV or their tautomers, solvates and/or pharmaceutically acceptable salts as described herein.

In another of its method aspects, this invention is directed to a method for treating a disorder, mediated at least in part by xanthine oxidase, which method comprises administering to a patient in need of the treatment an effective amount of one or more compounds of Formula IA, I, II, III, or IV or their tautomers, solvates and/or pharmaceutically acceptable salts.

Disorders mediated at least in part by xanthine oxidase include, but are not limited to, those selected from the group consisting of gout, hypoxia, and complications thereof Other disorders or conditions treatable by xanthine oxidase include by way of example tumor lysis syndrome associated with tumor chemotherapy, or allopurinol hypersensitivity syndrome;

ischemia-reperfusion injury such as ischemic bowel injury, myocardial ischemia-reperfusion injury, myocardial infarction, stroke, splanchnic ischemia-reperfusion injury, gut reperfusion injury, ischemia-reperfusion of liver, kidney, lung, other organs and whole body;

Circulatory shock, hemorrhagic shock, hepatic damage, vascular injury and progressive hemodynamic decompensation;

Chronic heart failure;

Hypertension, hypercholesterolemia, atherosclerosis, diabetes;

Inflammatory bowel diseases and other inflammatory diseases;

Rheumatoid arthritis;

Sickle cell disease;

Pneumonia;

Acute respiratory distress syndrome;

Chronic obstructive pulmonary disease;

Pancreatitis;

Peritonitis and peritoneal adhesions;

Uveitis;

Dermatitis; and

Various forms of toxic organ injury, including various forms of liver injury, e.g., ones induced by ionizing radiation, ethanol, cocaine, thioacetamide, acetaminophen, and aluminum.

The compounds of this invention are useful in the diagnosis and treatment of a variety of human disorders including, but are not limited to, those selected from the group consisting of gout, hypoxia, and complications thereof. For example, the compounds of the present invention are particularly useful in treating disorders such as gout and other disorders arising therefrom.

Compounds of this invention have improved safety and potency, such as the potency of inhibiting xanthine oxidase at low micromolar and even nanomolar concentrations.

The expression "effective amount," when used to describe an amount of compound in a method, refers to the amount of a compound that achieves the desired pharmacological effect or other effect, for example, an amount that results in uric acid production reduction. The compounds and compositions described herein or pharmaceutically acceptable salts thereof are useful for treating gout, hypoxia, or hyperuricemia in humans, including, without limitation, pediatric and geriatric populations, and in animals, e.g., veterinary applications. Optionally, the methods are used to treat conditions associated with elevated uric acid levels, including chronic gouty arthritis, acute inflammatory arthritis, uric acid nephropathy, kidney stones, or tophi.

In another of its method aspects, this invention is directed to a method for the treatment of patients having a condition due at least in part to over-sensitivity to uric acid by reducing the production of uric acid which method comprising administering to a patient in need of the treatment an effective amount of one or more compounds of Formula IA, I, II, III, or IV or their tautomers, solvates and/or pharmaceutically acceptable salts. In some embodiments, the patient has gout.

The methods described herein can further comprise administering to the subject a second therapeutic agent. Thus, the provided compositions and methods can include one or more additional agents. The one or more additional agents and the compounds described herein or pharmaceutically acceptable salts thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts thereof. The administration of the one or more additional agents and the compounds described herein or pharmaceutically acceptable salts thereof can be by the same or different routes and concurrently or sequentially.

Therapeutic agents include, but are not limited to, anti-gout agents. For example, the anti-gout agent can be allopurinol, benzbromarone, colchicine, probenecid, or sulfinpyrazone. Therapeutic agents also include anti-inflammatory agents. Examples of suitable anti-inflammatory agents include, for example, steroidal and nonsteroidal anti-inflammatory drugs (e.g., ibuprofen and prednisone). The therapeutic agent can also be, for example, an antioxidant. Examples of suitable antioxidants include, for example, α-tocopherol, beta-carotene, butylated hydroxyanisole (BHA), butylated hydroxytoluene (BHT), caffeic acid, lutein, lycopene, selenium, tert-butylhydroquinone (TBHQ), Vitamin A, Vitamin C, and Vitamin E. Further examples of suitable antioxidants include putative antioxidant botanticals, such as, for example, grape seeds, green tea, Scutellaria baicalensis, American ginseng, ginkgo biloba, and the like.

In addition, non-human uric acid enzymes that degrade uric acid can be used as a complementary therapy. Thus, in another aspect, there is provided a method for treating hyperuricemia, or a condition related thereto, by co-administration of a xanthine oxidase inhibitor described herein in combination with an effective amount of an enzyme that degrades uric acid. Examples of such enzymes are described in, e.g., WO 2007052326.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of gout or hyperuricemia), during early onset (e.g., upon initial signs and symptoms of gout or hyperuricemia), or after the development of gout or hyperuricemia. Prophylactic administration can occur for several days to years prior to the manifestation of symptoms of gout or hyperuricemia. Therapeutic treatment involves administering to a subject a therapeutically effective amount of the compounds and compositions or pharmaceutically acceptable salts thereof as described herein after gout or hyperuricemia is diagnosed.

The amount of active compound administered will vary depending upon the disease treated, the mammalian species, and the particular mode of administration, etc. Suitable doses for the compounds of the present invention can be, for example, between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. In some embodiments, the total dosage for a 70 kg adult is in the range of 0.001 to about 15 mg per kg weight of subject per administration or 0.01 to about 1.5 mg per kg weight of subject per administration, and such therapy can extend for a number of days, a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

Kits

Also provided herein are kits for treating or preventing gout or hyperuricemia in a subject. A kit can include any of the compounds or compositions described herein. For example, a kit can include a compound of Formula I or any of the compounds described herein. A kit can further include one or more additional agents, such as anti-gout agents (e.g., allopurinol, benzbromarone, colchicine, probenecid, or sulfinpyrazone), anti-inflammatory agents, or antioxidants. A kit can include an oral formulation of any of the compounds or compositions described herein. A kit can additionally include directions for use of the kit (e.g., instructions for treating a subject), a container, a means for administering the compounds or compositions, and/or a carrier.

Preparation of the Compounds of the Invention

The compounds described herein can be prepared by methods described herein or in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the temporary protection and deprotection of various chemical functional groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

In one aspect, the compounds described herein may be obtained, where available, from commercial sources. Some of the compounds herein can be obtained from, for example, Sigma Chemical Co. (St. Louis, Mo.), VWR International (Radnor, Pa.), or Oakwood Products, Inc. (West Columbia, S.C.).

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

It will be understood that particular syntheses described herein are shown by way of illustration and not as limitations on the syntheses of differently substituted aryl compounds. Those skilled in the art will recognize, or be able to ascertain using no more than routine experimentation, numerous equivalents or synthetic strategies in order to the make the aryl compounds described herein. Such synthetic methodologies are considered to be within the ability and knowledge of one skilled in art and are contemplated by the inventors of this application.

In one general embodiment, the synthesis of compounds of the invention may involve, first, treating a phenol with an electrophile in order to direct the placement of substituent(s), X-Lg, wherein Lg is a leaving group such as halo. Next, the arene is formylated. Finally, the arene undergoes a nitration reaction and the methylene alcohol is oxidized (Scheme 1).

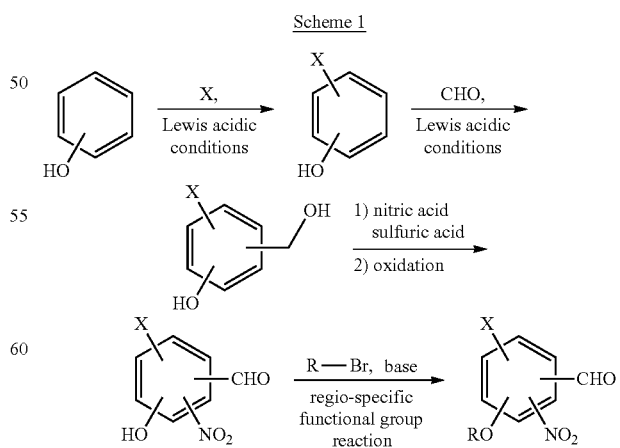

It is within the purview of the skilled artisan to combine steps in terms of functional group manipulation. For instance, selective functionalization of the phenol moiety, if desired, may occur in the first step and then that functionality may be carried thru to the end of the synthesis.

Compounds of the invention can be readily prepared from substituted benzaldehydes, particularly useful are 2,4-dihydroxybenzaldehyde, 3,4-dihydroxybenzaldehyde, and salicylaldehyde. A skilled artisan would appreciate that the reactivity of the phenol groups and the aldehyde are each different so that selectivity can be achieved by selecting suitable reagents and suitable reaction conditions for one of them to react but leaving the other intact to form the desired product.

In another general embodiment, the synthesis of the compounds of the invention involves transforming substituted-arene compounds by either electrophilic aromatic substitution or nucleophilic aromatic substitution. Such reactions are well known in the art and strategies have been developed to overcome problems in transforming arenes regardless of their substitution pattern. The skilled artisan will be able to transform various functional groups to match the desired reactivity with the desired substitution.

For example, as shown in Scheme 2,3,4-dihydroxybenzaldehyde is transformed into the 2-nitro substituted and 3-nitro substituted aryl compound by altering reaction conditions.

Accordingly, the skilled artisan can devise strategies, which may or may not utilize functional group transformations in order to change reactivity at certain spots on the aryl ring, in order to place any such desired functional group at any carbon on the aryl ring. Thus, in order to attach different functional groups on each position on the ring, each phenol moiety, or even in lieu of the aldehyde group, suitable protecting groups are well known in the art (see T. W. Greene, P. G. M. Wuts, Protective Groups in Organic Synthesis, 4th Edition, Wiley-Interscience, New York, 2006).

In an alternative aspect, the compounds of the invention can also be readily prepared from the following starting materials: 3,4-dihydroxy-5-nitrobenzaldehyde, 3,4-dimethoxybenzyl alcohol, 3,4-dihydroxyphenyl ethanol, 3,4-dihydroxyphenyl ethanol, 3,4,5-trihydroxybenzaldehyde hydrate, 4-hydroxy-3-methoxybenzyl alcohol, 3,4-dihydroxybenzoic acid, 3,4-dihydroxy-6-nitrobenzaldehyde, 2,4-dihydroxy-benzaldehyde, 4-hydroxy-benzaldehyde, 3-hydroxy-benzaldehyde, and salicylaldehyde. by methods known to one of skill in the art. Further, a skilled artisan would be able to modify readily available arene compounds and perform any necessary reactions to get the desired substitution pattern on the ring in order to obtain starting material for the synthesis of the compounds of this invention.

In one aspect, certain compounds of Formula I, II, III, and IV can be prepared according to methods illustrated in Scheme 3 wherein the variables are as defined in Formula I unless otherwise stated:

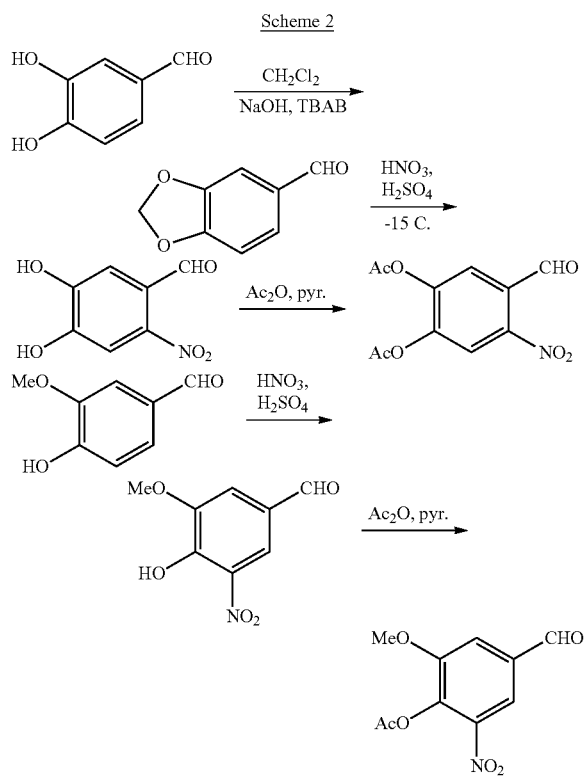

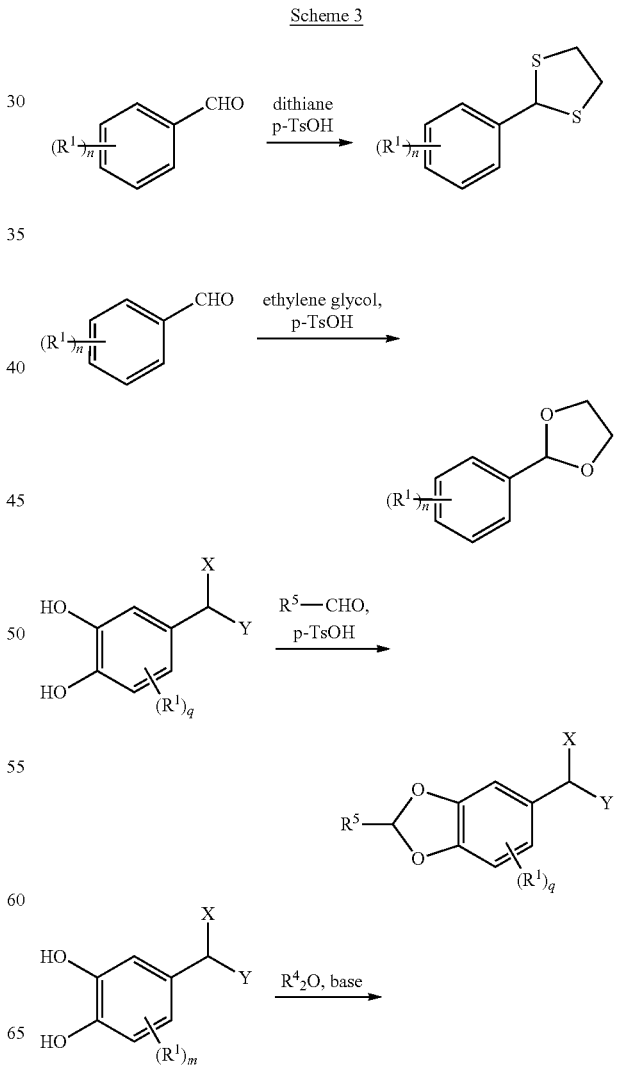

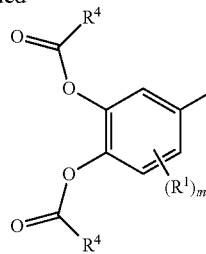
m is 0, 1, 2 or 3
In one aspect, certain compounds of Formula I, II, III, and IV can be prepared according to methods illustrated in Scheme 4:
Scheme 4
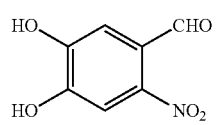
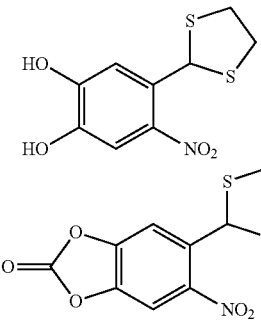
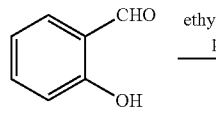
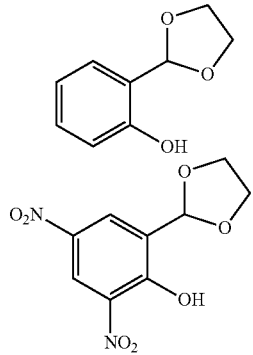
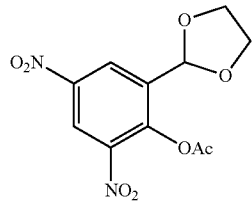
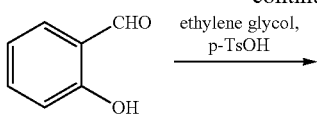
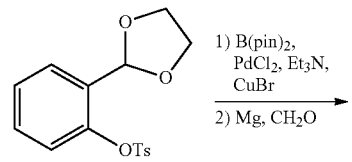
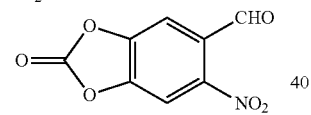
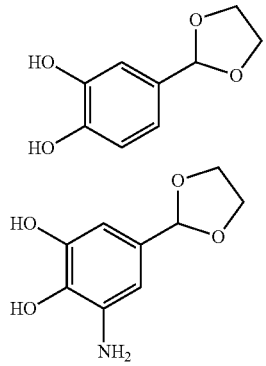
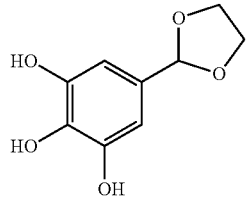
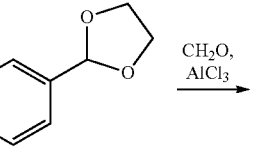
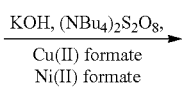

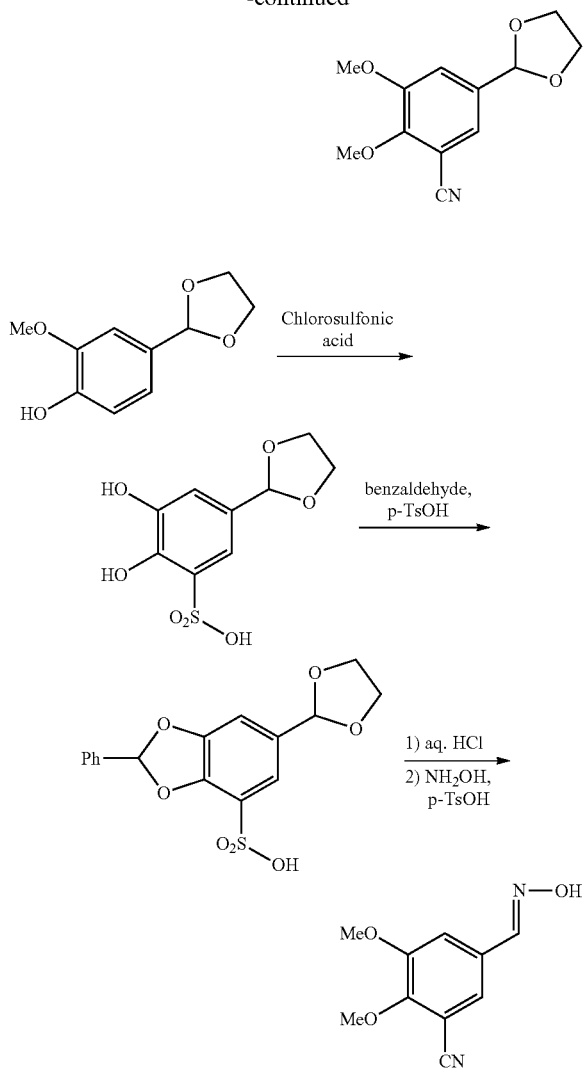

Certain starting compounds that can be used to prepare compounds of this invention include, but certainly are not limited to: 3,4-dihydroxy-5-nitrobenzaldehyde, 3,4-dimethoxybenzyl alcohol, 3,4-dihydroxyphenyl ethanol, 3,4-dihydroxyphenyl ethanol, 3,4,5-trihydroxybenzaldehyde hydrate, 4-hydroxy-3-methoxybenzyl alcohol, 3,4-dihydroxybenzoic acid, and 3,4-dihydroxy-6-nitrobenzaldehyde.

The preceding reaction schemes and syntheses are illustrative, but by no means the only way the compounds of the invention can be made.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the subject matter described herein which are apparent to one skilled in the art. Unless otherwise stated, all temperatures are in degrees Celsius (° C.).

In the examples below, the following abbreviations have the following meanings. If an abbreviation is not defined, it has its generally accepted meaning
MS=mass spectrometry
g=gram
h=hours
HCl=hydrochloric acid
HPLC=high-performance liquid chromatography
M=molar
mg=milligrams
ml or mL=milliliters
min=minutes
mM=micromolar
mmol=millimols
mU/ml=milliunit(s) per milliliter
m/z=mass to charge ratio
NaOH=sodium hydroxide
nM=nanomolars
nm=nanometers
UV=ultraviolet
wt %=weight percent
μM=micromolar Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Xanthine oxidase from bovine milk, xanthine, allopurinol, 3,4-dihydroxybenzaldehyde, phosphate buffered saline (PBS) solution, potassium nitrite ($KNO_2$), dioxide manganese ($MnO_2$), diethylene-triamine-pentaacetic acid (DTPA), EDTA, ferrous ammonium sulfate, hydrogen peroxide ($H_2O_2$), sodium hypochlorite, DPPH, 5,5'-dithio-bis(2-nitrobenzoic acid) (DTNB), sodium borohydride, potassium persulfate, ascorbic acid, and (±)-α-tocopherol were obtained from Sigma Chemical Co. (St. Louis, Mo.). 3,4-Dihydroxy-5-nitrobenzaldehyde, 3,4-dimethoxybenzyl alcohol, 3,4-dihydroxyphenyl ethanol, caffeic acid, 3,4-dihydroxyphenyl ethanol, 3,4,5-trihydroxybenzaldehyde hydrate, 4-hydroxy-3-methoxybenzyl alcohol, and 3,4-dihydroxybenzoic acid were obtained from VWR International (Radnor, Pa.). 3,4-Dihydroxy-6-nitrobenzaldehyde was obtained from Oakwood Products, Inc. (West Columbia, S.C.).

Data are presented as mean±SD as compared to the negative control. Statistical significance was determined by a Student's t-test (two tailed). A value of $P<0.05$ was considered significant.

Example 1

XO Inhibition Assay

XO activity was determined by the method of continuous spectrophotometric rate determination by monitoring the increase of absorption at 295 nm of uric acid in 67 mM phosphate buffer (pH 7.4) containing 20 nM xanthine oxidase with an activity of 5 mU/ml, with or without the compounds as described herein. After pre-incubation for 1 to 5 min at 25° C., the formation of uric acid in the reaction mixture was initiated by the addition of 50 µM xanthine. The test compounds and positive control are shown in Scheme A. Allopurinol was used as a positive control. All compounds, including allopurinol, were dissolved in H$_2$O or an aqueous solution. H$_2$O was used as the negative control.

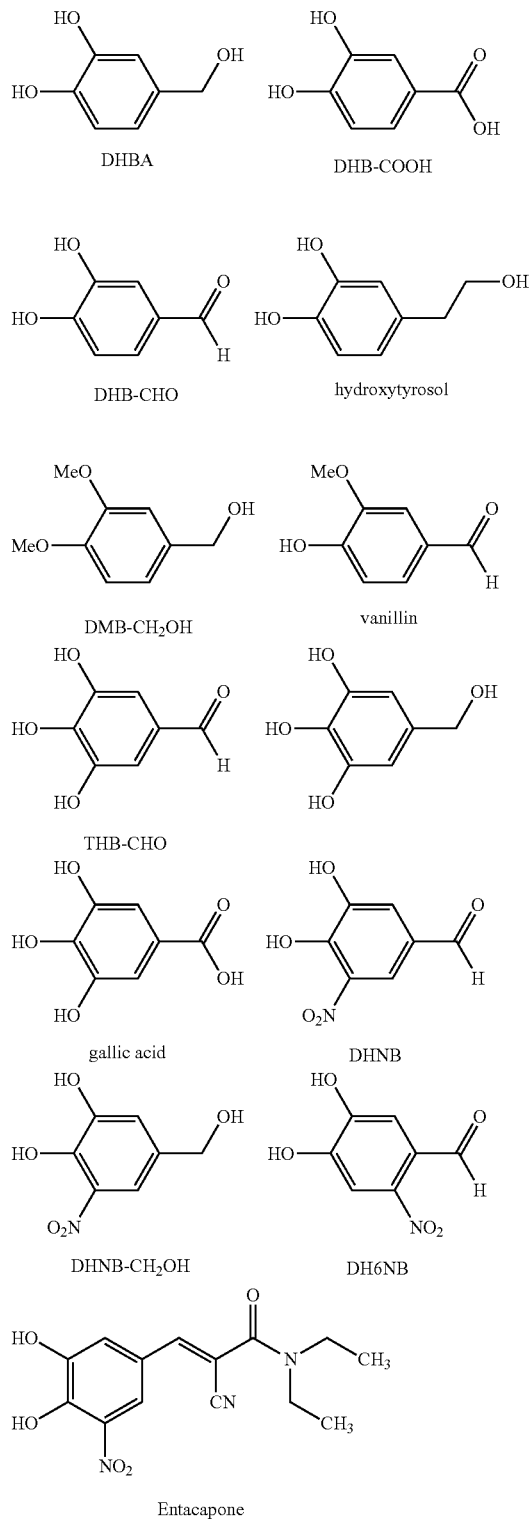

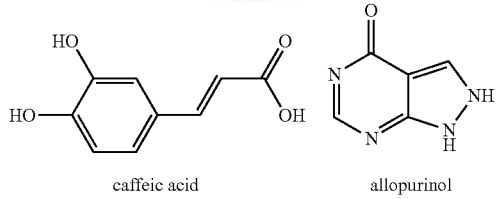

Figure 1B:
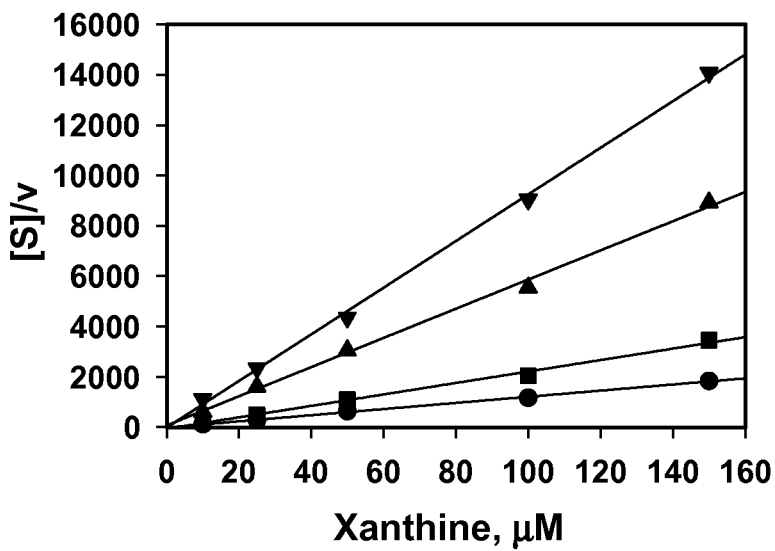
FIG. 1B is a Dixon Plot for DHNB at varying concentrations of xanthine.
Figure 1C:
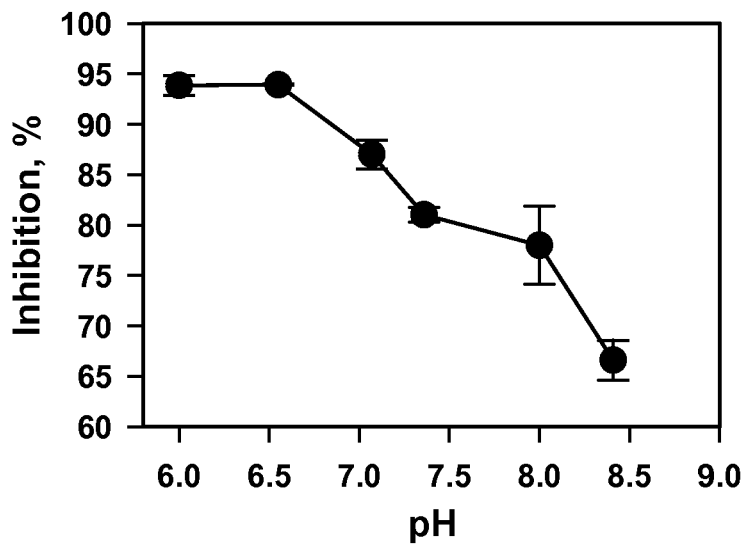
FIG. 1C is a graph showing the effects of pH on the inhibitory effect of DHNB on XO.

XO inhibition—The inhibitory activity of xanthine oxidase by DHNB, DHBA, DH6NB and THB-CHO was determined in vitro by the formation of uric acid, which was measured spectrophotometrically by following the increase in absorbance of uric acid at 295 nm. When 20 nM XO was mixed with increasing concentrations of allopurinol, DHNB, DH6NB, DHBA, or THB-CHO (Scheme A), the initial rate of uric acid formation showed a concentration-dependent decrease compared to the control, reflecting the decrease of XO activity (see FIG. 1A). DHNB significantly inhibited XO activity with an IC$_{50}$ value of 3 µM, which is close to allopurinol's value of 1.8 µM. The IC$_{50}$ values for DHBA and DH6NB were 76 and 96 µM, respectively, indicating weak inhibition of XO activity. The IC$_{50}$ value for THB-CHO was too high to determine. After DHNB and XO were pre-incubated for 1 min, xanthine was added to initiate the reaction. The initial rate of uric acid formation did not change with increasing concentrations of xanthine. A Dixon plot of a steady-state kinetic study of DHNB inhibition on XO activity indicated that the initial rates did not change with increasing xanthine concentrations when the concentration of DHNB was fixed (see FIG. 1B). The pH dependence of DHNB inhibition indicated that neutral or slightly acidic solutions benefit the inhibition (see FIG. 1C).

Figure 2:
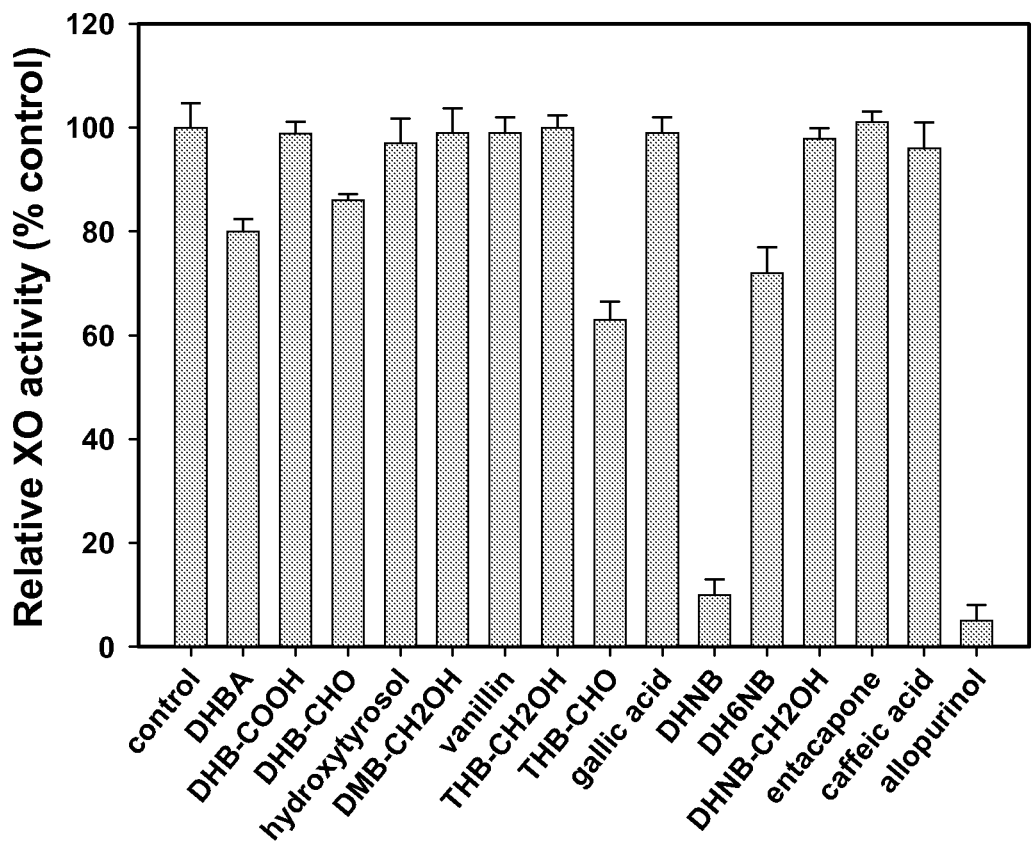
FIG. 2 is a graph comparing the xanthine oxidase inhibitory effects of catechol compounds, each at a concentration of 20 µM. The control represents no inhibitor added.

Structure activity relationship of XO inhibition—The inhibition of XO activity by the other compounds shown in Scheme A, including a drug entacapone, was also studied. These compounds possess the same catechol skeleton in their structures but with different functional groups. The ability of each compound to inhibit XO at a concentration of 20 µM was compared with that of allopurinol (see FIG. 2). Although these compounds have similar structures, their XO inhibition capacities were different. Compounds containing a —CHO group, such as DHNB, DH6NB, DHB-CHO and THB-CHO, had inhibitory effects on XO. Vanillin, although containing a —CHO group, had no inhibition on XO activity. DHBA has no —CHO group but it showed moderate inhibition. Other compounds, such as DHB-COOH, gallic acid, caffeic acid, hydroxytyrosol, DMB CH$_2$OH and DHNB-CH$_2$OH, containing —COOH or —CH$_2$OH, had no effect on XO. Entacapone, the catechol-O-methyl transferase (COMT) inhibitor, did not show any inhibitory effect on XO even though it possesses a 3,4-dihydroxy-5-nitrobenzyl moiety, as does DHNB, the strong XO inhibitor.

Figure 3:
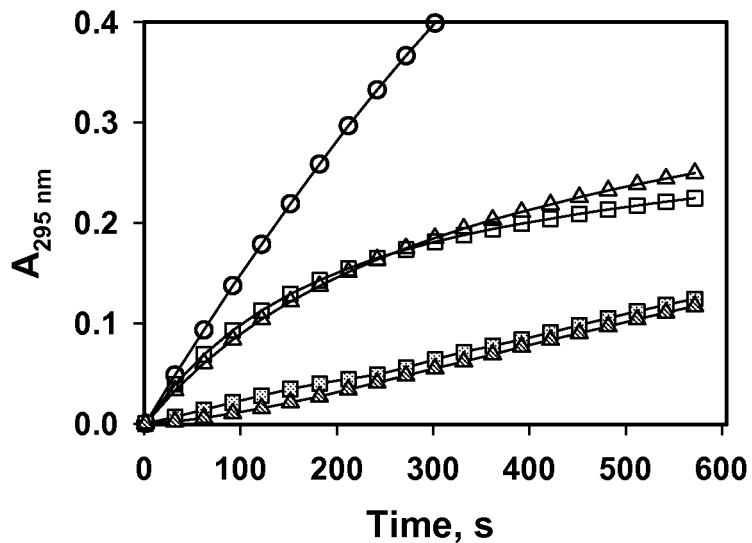
FIG. 3 is a graph showing the time course of inhibition of xanthine oxidase activity by DHNB and allopurinol. XO activity was determined under standard conditions and started by adding 20 nM XO (open symbols) or by adding 50 µM xanthine following 4 min pre-incubation of XO and inhibitor (solid symbols). Circles, control—no inhibitor added; squares, with 6.67 µM allopurinol; triangle, with 6.67 µM DHNB.

XO inhibition of DHNB is irreversible—DHNB displayed time-dependent inhibition of XO activity, similar to that of allopurinol. When XO (20 nM) was added to the mixture of xanthine (50 µM) and the inhibitor (6.67 µM) to start the reaction, both DHNB and allopurinol showed time-dependent inhibition (see FIG. 3). An excess of 6.67 µM DHNB or 6.67 µM allopurinol reduced the rate gradually and finally reached a steady state level of catalytic activity. No complete inactivation was observed at the tested condition. After pre-incubation of 20 nM XO with 10 µM DHNB or 10 µM allopurinol for 4 min, the catalytic activity of XO displayed a steady state from the beginning and both DHNB and allopurinol showed a similar inhibitory pattern.

Figure 4:
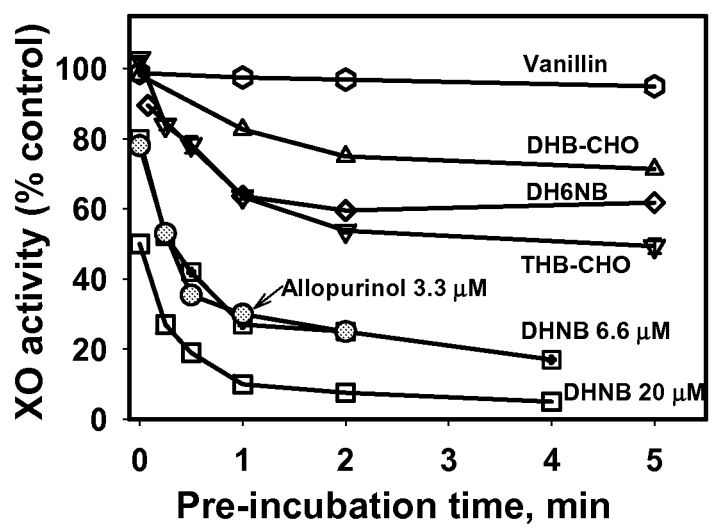
FIG. 4 is a graph showing the influence of pre-incubation of 20 µM inhibitors with 20 nM XO on XO activity. Vanillin, DHB-CHO, DH6NB, THB-CHO, allopurinol (at 3.3 µM), and DHNB (at 6.6 µM and 20 µM) were the tested compounds.
Figure 5:
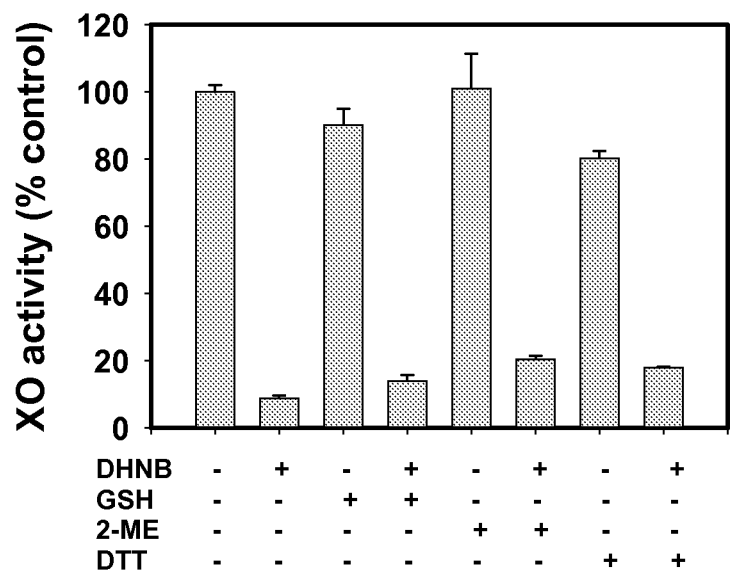
FIG. 5 is a graph demonstrating that DHNB inhibition of XO is not reversible by reducing agents. XO (10 mM/ml) and 20 µM DHNB were pre-incubated for 10 min at 25° C. in phosphate buffer (100 mM pH 7.4). Then a high level of GSH (20 mM), 2-mercaptoethanol (2-ME, 20 mM), or dithiothreitol (DTT, 20 mM) was added for 15 min, and XO activity was analyzed by the production of uric acid. A "+" signifies the addition of the reagent DHNB, GSH, 2-ME, and/or DTT. A "−" signifies that the reagent was not added. Data represent the mean±S.E. at least three independent determinations.

Furthermore, after preincubation of the DHNB and XO for 0 to 5 min at 25° C., the formation of uric acid in the reaction mixture was initiated by the addition of 50 µM xanthine. Pre-incubation of the DHNB and XO significantly increased the inhibition. For example, 6.67 µM DHNB only inhibited 20% of XO activity without pre-incubation, as determined by comparing with the control of the initial rate in the first 200 s. However, after a 2-min incubation of DHNB and XO, the inhibition was increased to 75%. Meanwhile, pre-incubation also affected the XO inhibition of DH6NB, DHB-CHO, and THB-CHO (see FIG. 4). The inhibition of DHB-CHO on XO activity was not concentration dependent but instead was pre-incubation time dependent. However, pre-incubation of XO and DHBA did not increase the inhibition potency of DHBA. For other compounds listed in Scheme A, such as vanillin, DHB-COOH, hydroxytyrosol, DMB-$CH_2OH$, THB-$CH_2OH$, gallic acid, DHNB-$CH_2OH$, caffeic acid, and entacapone, pre-incubation with XO for up to 5 min did not show any inhibitory effect. These results indicate that DHNB is an irreversible XO inhibitor in the tested condition. Also, XO was treated with 20 µM DHNB to induce inhibition; the reaction mixture was then treated with high levels of glutathione (GSH; 20 mM), dithiothreitol (DTT; 20 mM) or 2-mercaptoethanol (2-ME; 20 mM), which did not abolish the inhibition (see FIG. 5).

Example 2

Conversion of DHNB to Products by XO

The reaction kinetics of DHNB with XO at different pH values were measured using a spectrophotometer by monitoring the decay of DHNB at 327 nm in a system of 30 nM XO with 30 µM DHNB in phosphate buffer with pH 6.5 to 8.5. The extinction coefficient of DHNB at 327 nm was measured as 15,600 $M^{-1}$ $cm^{-1}$. The sample for product analysis by mass spectroscopy and HPLC was prepared by mixing 0.3 U XO with 4 mg DHNB in 1 mL phosphate buffer (pH 7.4) for 3 days. The DHNB/XO samples were analyzed by HPLC (Bio-Rad BioLogic DuoFlow; Hercules, Calif.) equipped with a 250×4.6 mm, 5 micron Phenomenex C-18 (2) Luna column, with a mobile phase of 40% acetonitrile/water. DHNB and its product were monitored by the optical absorption at 279 nm and 327 nm.

Negative electrospray ionization-mass spectrometry (ESI-MS) and tandem (MSMS) were applied to detect and confirm the reaction products of DHNB with XO. All mass spectrometric experiments were performed on an API 3200-Qtrap triple quadrupole mass spectrometer (Applied Biosystem/MDS SCIEX; Foster City, Calif.) equipped with a TurbolonSpray™ source. The main working parameters for mass spectrum were set as follows: ion-spray voltage, −4.5 kV; ion source temperature, 600° C.; gas 1, 40 psi; gas 2, 40 psi; curtain gas, 20 psi; collision gas, high.

Reaction of XO and DHNB—To determine how DHNB inhibits XO enzyme activity, 30 µM DHNB was incubated with 15 mU/ml (or 30 nM) XO in phosphate buffer (pH 7.4) and xanthine was then added to initiate the reaction as discussed above. The inhibition of DHNB on XO activity lasted up to 20 h. After that, the enzymatic activity of XO was recovered. The optical spectral change of DHNB was measured in a system without xanthine, i.e., 30 µM DHNB with 15 mU/ml (or 30 nM) XO in phosphate buffer.

Figure 6A:
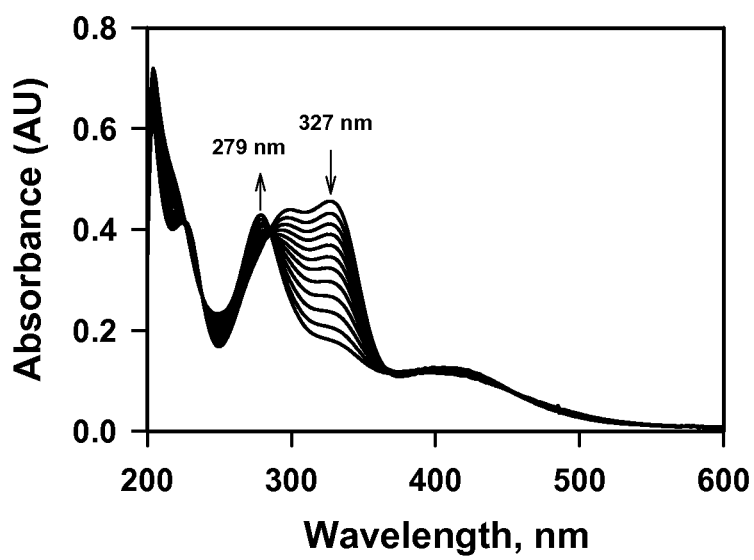
FIG. 6A is a graph of the time course of absorption change of DHNB (327 nm, arrow indicates decrease) and the formation of the product (279 nm, arrow indicates increase) following the mixing of 30 nM XO and 30 µM DHNB in 0.1 M phosphate buffer (pH 7.4).
Figure 6B:
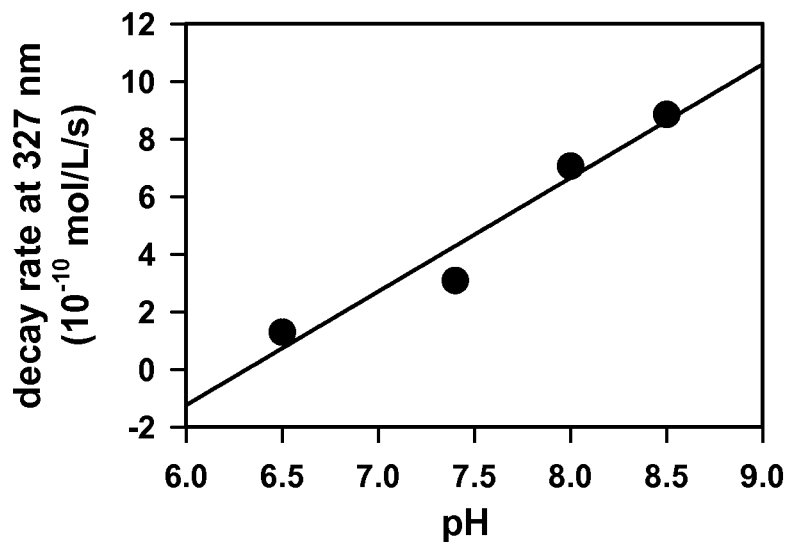
FIG. 6B is a graph showing the effects of pH on the conversion of DHNB by XO enzyme.

The absorption of DHNB at 327 nm decreased with time and a new peak appeared at 270 nm (see FIG. 6A). The decay rate was in the range of $10^{-10}$ mol/L/s and was pH dependent, i.e., the higher the pH value, the faster DHNB decayed (see FIG. 6B).

Figure 6C:
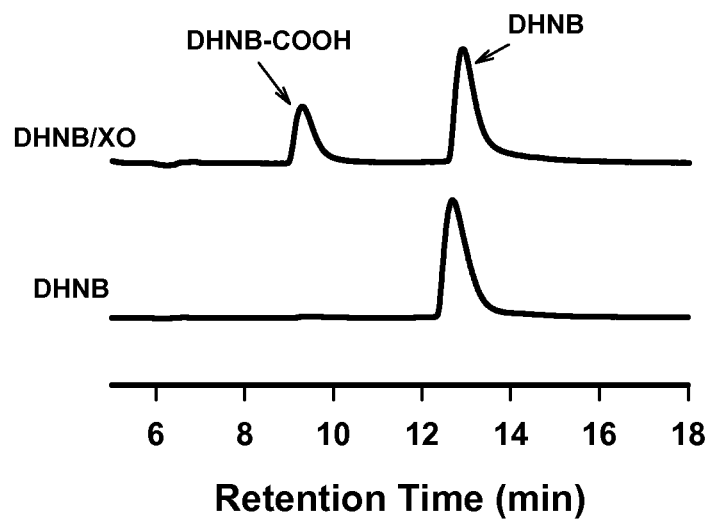
FIG. 6C contains an HPLC profile of DHNB (control) and a DHNB/XO mixture after incubation for 3 days.
Figure 6D:
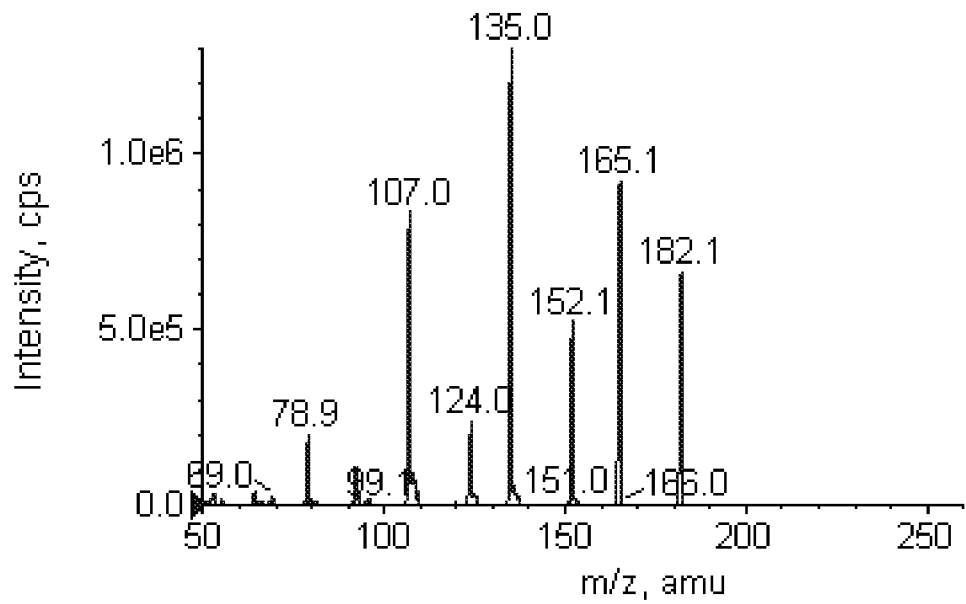
FIG. 6D is a MS/MS spectrum of DHNB.
Figure 6E:
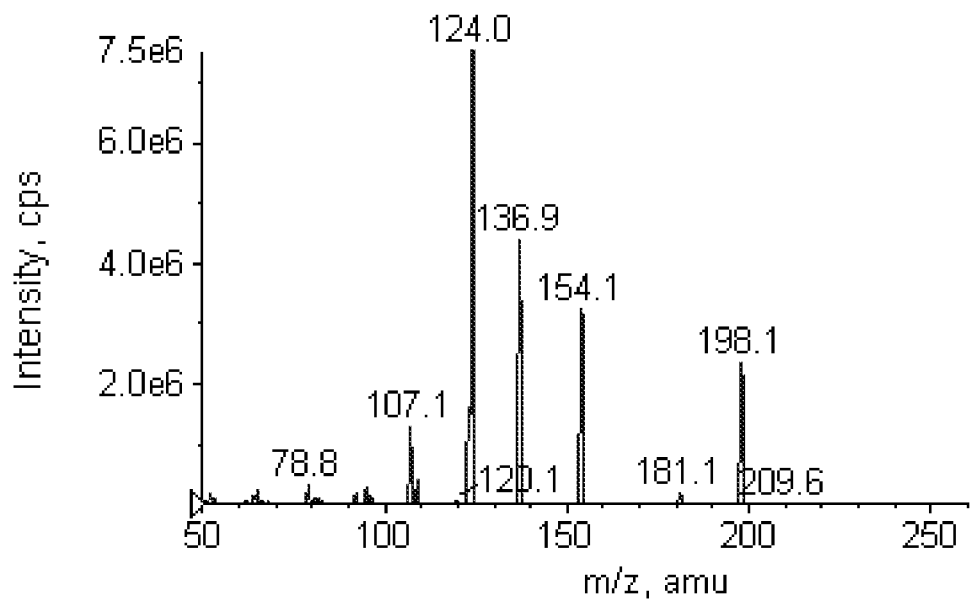
FIG. 6E is a MS/MS spectrum of the DHNB/XO product, DHNB-COOH.

Without XO, however, DHNB itself was very stable. At room temperature, DHNB was converted by XO enzyme to a product which has no inhibitory effect on XO and thus recovered the XO activity as the concentration of DHNB decreased. The UV-VIS spectrum of the product was different from that of DHNB. HPLC analysis of DHNB/XO showed a new peak which was more polar than DHNB (see FIG. 6C). Mass spectrometric analysis of the product gave a molecular ion ($[M-H]^-$) peak at m/z 198 in the EI mass spectrum, while DHNB showed $[M-H]^-$ peak at m/z 182 (see FIG. 6D, E). The MS/MS of m/z 182 of DHNB gave several typical fragments such as m/z 165 ($[M-H—OH]^-$), 152 ($[M-H—CHO—H]^-$) and 135 (m/z 152-OH). However, the MS/MS of molecular ion at m/z 198 of the product gave a first main fragment at m/z 154, a mass difference of 44 indicating a loss of $CO_2$, which further loses a —OH to give a fragment at m/z 137. Based on the mass spectrum, the product is 3,4-dihydroxy-5-nitrobenzoic acid, implying that DHNB is oxidized to the acid by the enzyme.

Example 3

Antioxidant Activity of DHNB

In addition, unlike allopurinol, the compounds described herein can serve as antioxidants. This was determined by testing the ability of the compounds to scavenge DPPH, HOCl, peroxynitrite, and the superoxide ion. Each experiment was performed three times and the data are presented as mean±SD.

DPPH scavenging assay—The abilities of the polyphenols described herein to scavenge the DPPH radical were measured optically by monitoring the decreases of their absorptions at 429 nm. The DPPH scavenging activities of DHNB, DH6NB, DHBA, DHB-CHO, THB-CHO, and allopurinol were assayed at a concentration of 20 µM (FIG. 7A). DPPH was used at a concentration of 100 µM. Their scavenging activities were compared with that of vitamin C. As shown in FIG. 7A, DHNB, DH6NB, DHBA, DHBCHO, and THB-CHO have as strong of a DPPH scavenging effect as vitamin C; however, allopurinol has no scavenging effect on DPPH. The concentration dependent effects of compounds DHNB, DHBA, DHB-CHO, and allopurinol on DPPH scavenging activity were also studied and compared with that of vitamins C and E (FIG. 8).

HOCl scavenging assay—HOCl was prepared immediately before use by adjusting the pH of a 1% (v/v) solution of NaOCl to pH 6.2 with 0.6 M sulfuric acid. The concentration was further determined spectrophotometrically at 235 nm using the molar extinction coefficient of 100 $M^{-1}$ $cm^{-1}$. 5-Thio-2-nitrobenzoic acid (TNB) was prepared by reducing 5,5'-dithio-bis(2-nitrobenzoic acid) (DTNB) with sodium borohydride in phosphate buffer. The final concentrations of reagents used in the assay are as follows: 25 µM HOCl, 70 µM TNB, 0 to 200 µM antioxidants, phosphate buffer, 50 mM, pH 6.6. The HOCl scavenging assay was based on the inhibition of TNB oxidation to DTNB induced by HOCl.

Figure 9:
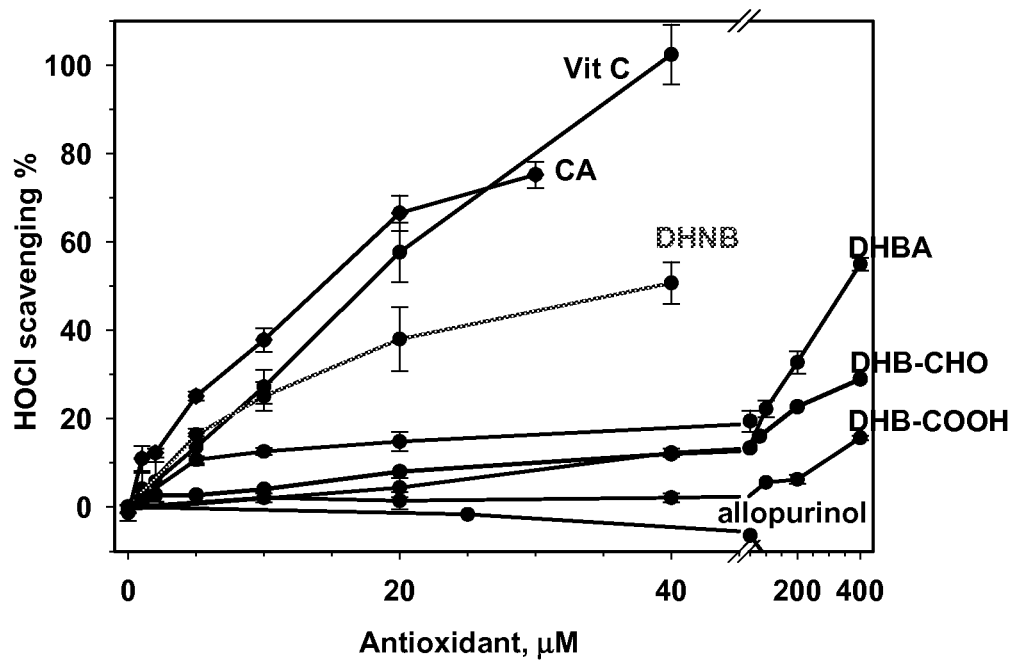
FIG. 9 is a graph showing the concentration dependent HOCl scavenging activities of DHNB, caffeic acid (CA), DHBA, DHB-CHO, DHB-COOH, and allopurinol. Vitamin C (Vit C) was used as a control.

At 20 µM, THB-CHO had a stronger HOCl scavenging effect than that of vitamin C. DHNB had a moderate scavenging effect, while other compounds, including DHBA, DHB-CHO, and DH6NB, had a weak scavenging effect on HOCl (FIG. 7B). The concentration dependent effect of these compounds, including DHNB, caffeic acid, DHBA, DHB-CHO, DHB-COOH, and allopurinol, on HOCl scavenging activity were also studied and compared with that of Vitamin C (FIG. 9).

Figure 10:
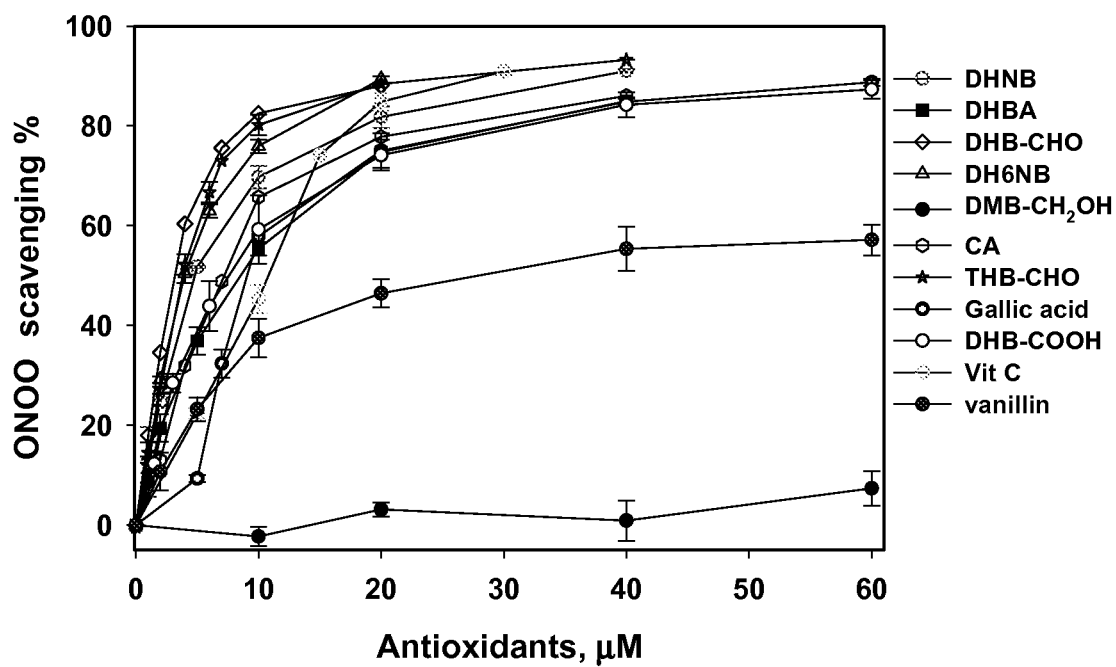
FIG. 10 is a graph showing the concentration dependent peroxynitrite scavenging activity of DHNB, DHBA, DHB-CHO, DH6NB, DMB-CH$_2$OH, caffeic acid, THB-CHO, gallic acid, DHB-COOH, and vanillin. Vitamin C (Vit C) was used as a control.

Peroxynitrite scavenging assay—Peroxynitrite (ONOO—) was generated by mixing 5 mL acidic solution (0.6 M HCl) of $H_2O_2$ (0.7 M) and 5 mL of 0.6 M $KNO_2$ in an ice bath for 1 second and the reaction was quenched with 5 mL of ice-cold 1.2 M NaOH. Residual $H_2O_2$ was removed using granular $MnO_2$ prewashed with 1.2 M NaOH and the reaction mixture was then left overnight at −20° C. Concentrations of ONOO− were determined before each experiment at 302 nm using a molar extinction coefficient of 1,670 $M^{-1}$ $cm^{-1}$. The final concentrations of reagents used in the assay are as follows: 25 µM ONOO−, 10 µM DTPA, 5 µM DHR 123, 0.1 M phosphate buffer, pH 7.4. The ONOO− scavenging assay was performed by monitoring the oxidation of dihydrorhodamine (DHR 123) by ONOO− spectrophotometrically at 500 nm. The abilities of DHNB, DHBA, DHB-CHO, DH6NB, caffeic acid, THB-CHO, gallic acid, vanillin, and DMB-CH2OH to scavenge peroxynitrite were compared with that of vitamin C. DHNB, DHBA, DHB-CHO, DH6NB, caffeic acid, THB-CHO and gallic acid had a strong scavenging effect on ONOO− (FIG. 7C). Vitamin C was used as a positive control. The concentration dependent effects of these compounds on ONOO− scavenging were also studied and compared with that of vitamins C and E (FIG. 10).

Superoxide scavenging assay—Superoxide ($O_2^{-\bullet}$) scavenging activity was assayed in the xanthine-xanthine oxidase system and determined by the inhibition of the reduction of nitro blue tetrazolium (NBT) to form blue formazan which has an absorption at 560 nm. The final concentrations of reagents used in the assay are as follows: 16.8 mU xanthine oxidase, 25 µM xanthine, 50 µM NBT, and 0.1 M phosphate buffer (pH 8.5). $O_2^{-\bullet}$ production and xanthine oxidase activity were measured as NBT reduction (at 560 nm) and uric acid production (at 295 nm), respectively. The abilities of polyphenols to scavenge $O_2^{-\bullet}$ were compared with that of GSH.

Figure 11:
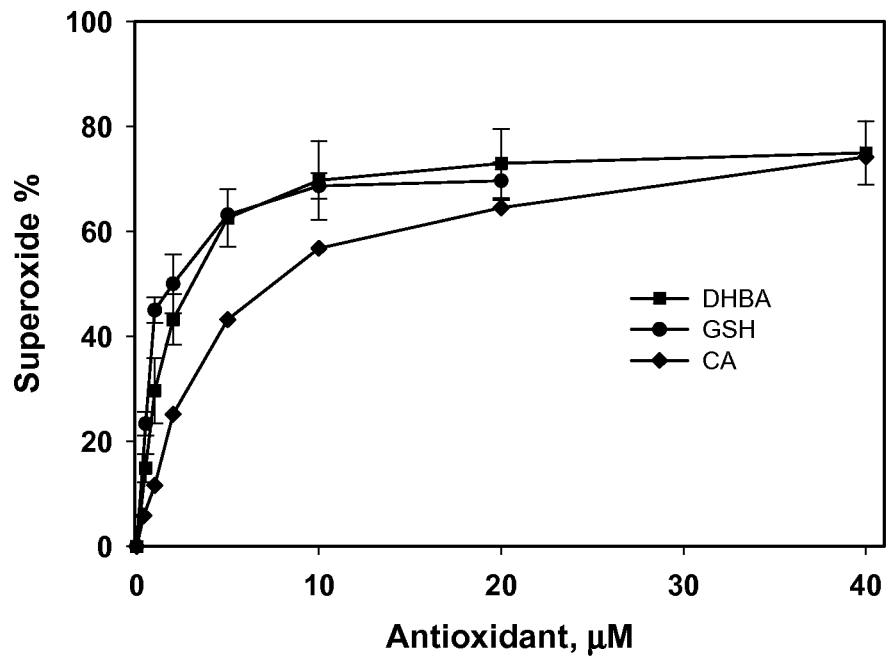
FIG. 11 is a graph showing the concentration dependent superoxide ion scavenging activity of caffeic acid and DHBA. Glutathione (GSH) was used as a control.

DHBA and THB-CHO, at the concentration of 20 µM, had strong scavenging effects on superoxide (FIG. 7D). DHBA had an even stronger superoxide scavenging effect than that of glutathione. The concentration dependent effect of DHBA and caffeic acid on superoxide scavenging was also studied and compared with that of glutathione (FIG. 11).

Figure 7:
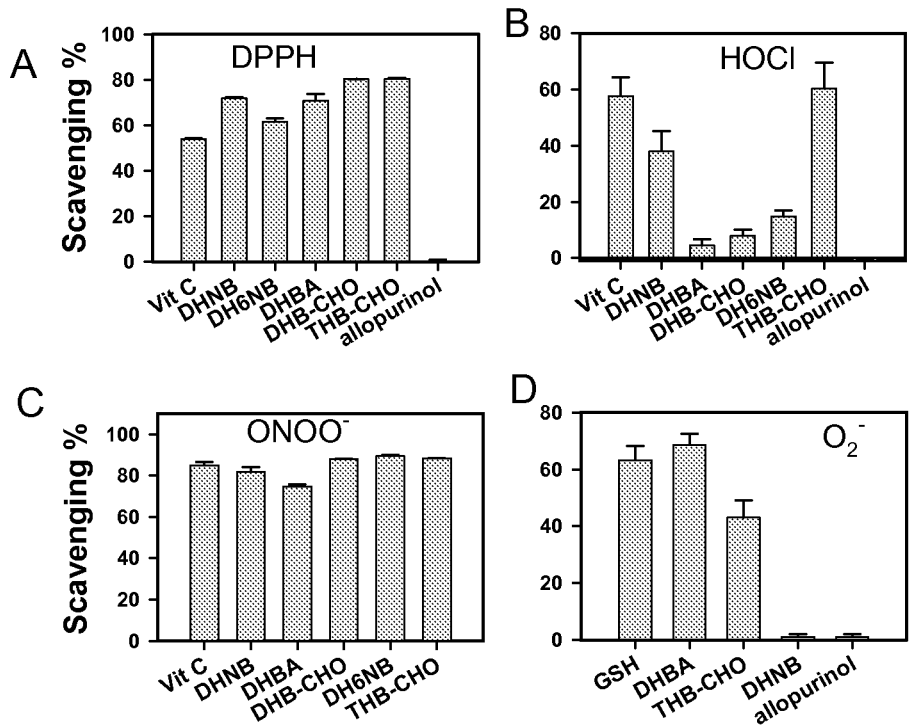
FIG. 7 contains graphs showing the antioxidant activities of DHNB, DH6NB, DHBA, DHB-CHO, THB-CHO, and allopurinol on the scavenging of free radical DPPH (panel A), hypochlorous acid (HOCl) (panel B), peroxynitrite (ONOO$^-$) (panel C), and/or superoxide ion ($O_2^{-\cdot}$) (panel D). Vitamin C (Vit C) or glutathione (GSH) was used as a control. Each compound was used at a concentration of 20 µM.
Figure 8:
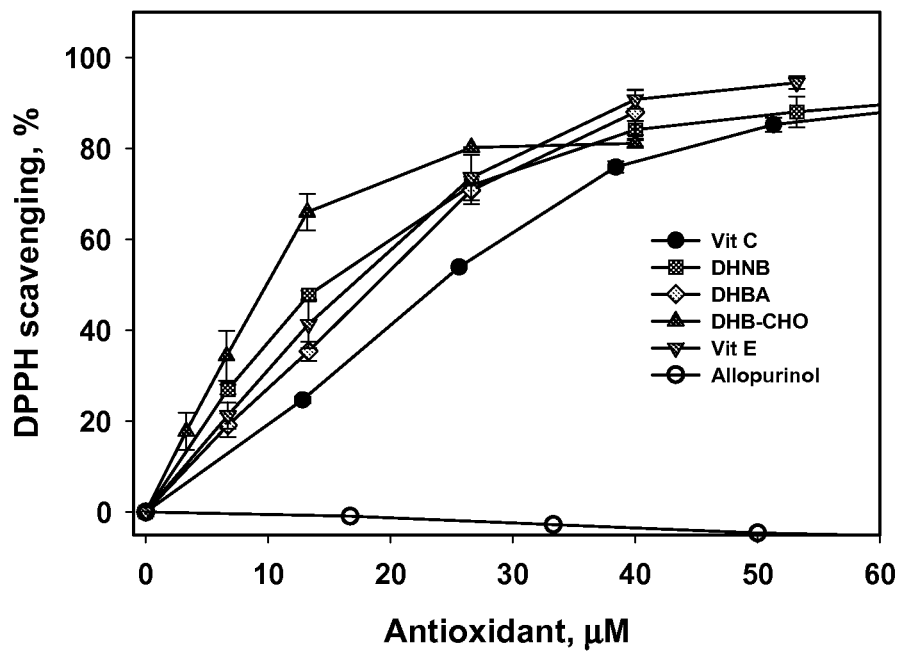
FIG. 8 is a graph showing the concentration dependent DPPH scavenging activities of DHNB, DHBA, DHB-CHO, and allopurinol. Vitamin C (Vit C) and Vitamin E (Vit E) were used as controls.

Antioxidant activity of Polyphenols—Several of the compounds described herein strongly scavenged DPPH, ONOO−, HOCl, and superoxide ion with low $IC_{50}$ values (see FIG. 7). Allopurinol does not possess the antioxidant properties similar to the compounds described herein. Thus, the antioxidant properties of the compounds described herein are an advantage as XO inhibitors over allopurinol.

Example 4

Hypouricemic Effect of DHNB in Allantoxanamide Induced Hyperuricemic Mice

A hyperuricemia mouse model was used. Allantoxanamide, a potent uricase inhibitor, was used to induce hyperuricemia in mice in this study. Briefly, adult C57BL/6 mice (15-25 g, 6-8 weeks old, 6 per group) were administrated DHNB at a concentration of 100 mg/kg in 1.0% polyethylene glycol 400 (PEG400 in a volume of 0.1 ml/10 g mouse body weight) via oral gavage. The mice were subsequently intraperitoneally injected with allantoxanamide at 200 mg/kg in 0.5% CMC-Na in a volume of 0.1 ml/10 g mouse body weight just after the tested drug oral administration to increase the serum uric acid level. Positive control mice were administered allopurinol at the same concentration as DHNB followed by i.p. allantoxanamide. The negative control mice were administered PEG400 only followed by i.p. allantoxanamide. The normal group mice were administered PEG400 only followed by i.p. CMC-Na only. Food and water were withheld overnight prior to the study. Whole blood samples were collected from mice through orbital vein bleeding at the end of the study. The mice were anaesthetized with diethyl ether inside a chamber. The blood was allowed to clot for 1 h at room temperature and then centrifuged at 2350×g for 4 min to obtain the serum. The serum was kept on ice and assayed immediately. Serum uric acid was determined with the phosphotungstate method, as known to those of skill in the art.

Figure 12:
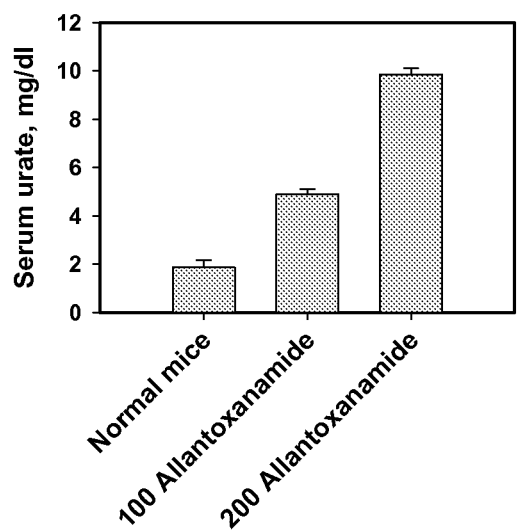
FIG. 12 is a graph showing the dose dependent hyperuricemic effects of allantoxanamide in mice.
Figure 13:
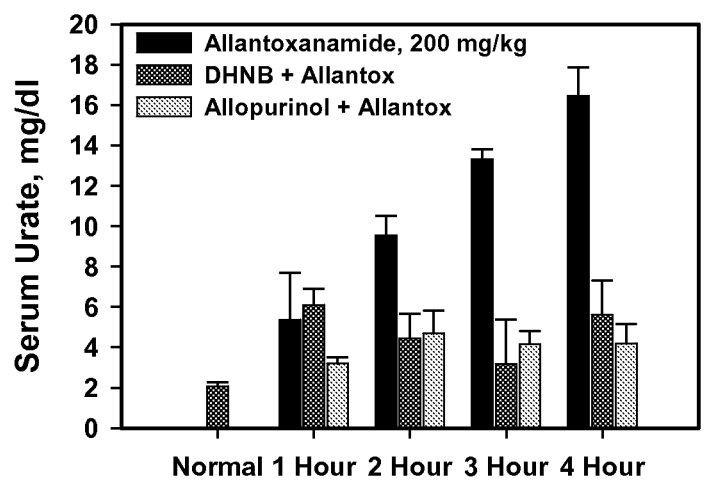
FIG. 13 is a graph showing the time course of the hypouricemic effect of DHNB and allopurinol on the allantoxanamide induced hyperuricemic mice.

Both allantoxanamide and potassium oxonate have been used as uricase inhibitors; however, the hyperuricemic effects of allantoxanamide are stronger and last longer than that of oxonate in rats. A single intraperitoneal injection of 200 mg/kg allantoxanamide in mice progressively increased the serum acid level during the experiment for 4 hours. The serum urate levels were elevated from 2 mg/dl (normal mice) to 5.4, 9.5, 13.3, and 16.4 mg/dl in 1, 2, 3, and 4 h after the allantoxanamide i.p. injection, respectively. In contrast, when the mice were orally administered 100 mg/kg DHNB before the allantoxanamide injection, the serum urate levels were significantly lowered in 2 hours and maintained at a level just slightly higher than the normal level in 4 hours. In comparison, when allopurinol was used in the same condition as that of DHNB, allopurinol also significantly lowered the serum urate level close to the normal level in mice. See FIG. 12 and FIG. 13.

Example 5

Acute Toxicity Studies of DHNB in Mice

To determine whether DHNB has any acute toxicity in mice, C57BL/6 mice were randomized into 3 groups (12/group). Groups 1 to 3 received an oral vehicle solution (PEG400), DHNB (500 mg/kg), and allopurinol (500 mg/kg), respectively. Each mouse was monitored for general health conditions on a daily basis for 28 days, including examination of mortality, body weights, and behavior of the mice.

Figure 14A:
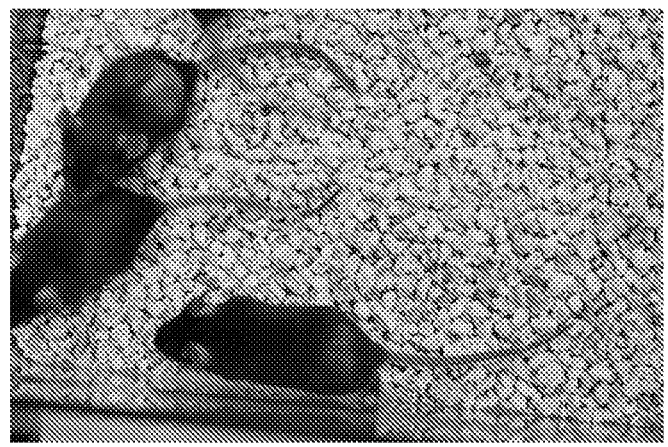
FIG. 14A is a photograph of allopurinol treated mice at 2.5 weeks.
Figure 14B:
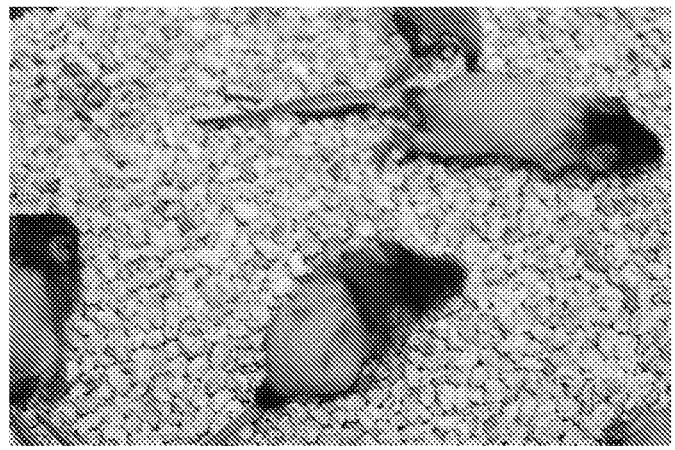
FIG. 14B is a photograph of allopurinol treated mice at 3 weeks.
Figure 14C:
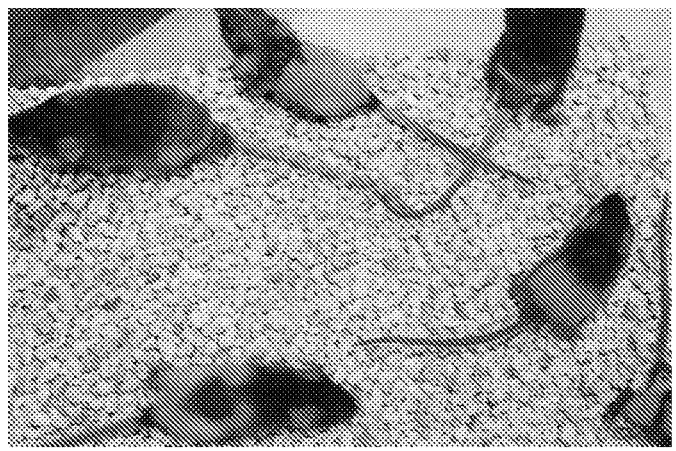
FIG. 14C is a photograph of allopurinol treated mice at 4 weeks.
Figure 14D:
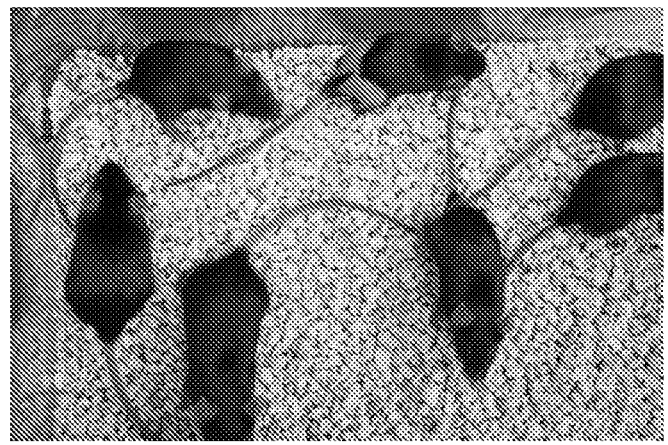
FIG. 14D is a photograph of allopurinol treated mice at 6 weeks.
Figure 14E:
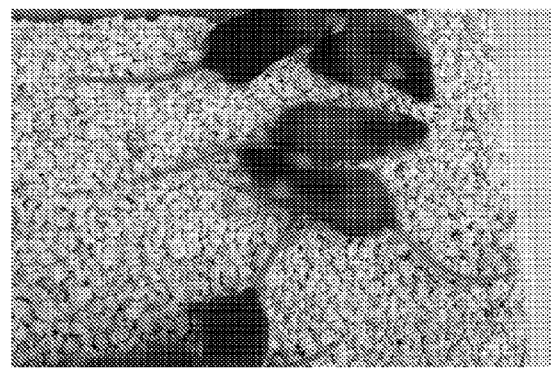
FIG. 14E is a photograph of DHNB treated mice at 4 weeks.

Toxic effects of DHNB are not reported, but the lowest published lethal dose of DHNB in the mouse is 312 mg/kg (oral administration once). DHNB or allopurinol at 500 mg/kg was administrated to 12 mice, respectively, via oral gavage. Control mice received the vehicle solution. The animals were observed daily up to 28 days. DHNB-treated mice did not show any symptoms of general toxicity. There was no difference in body weight and behavior between DHNB-treated mice and control mice. Histology analysis for the liver, kidney, and heart did not show any difference between DHNB-treated mice and control mice. In the allopurinol treated mice, however, 5 mice died within 3 days (mortality 42%). Furthermore, the surviving mice (mixed male and female) gave birth to total 19 pups, but eight died in two days. The survived pups of allopurinol treated mice started to lose hair after two weeks (FIG. 14A) and lost most of the back hair at 3 weeks (FIG. 14B) to 4 weeks (FIG. 14C). After separated from the adult mice, the pups started to grow hair again and returned to normal hair at the age of 6 to 7 weeks (FIG. 14D). However, this hair loss phenomenon was not observed on DHNB treated mice (see FIG. 14E for DHNB treated mice at 4 weeks). A summary of the in vivo toxicities of DHNB and allopurinol in mice is shown in Table 1.

TABLE 1

| 12 Mice/group | | Behavior | Organs | Mortality | 2nd Generation Mortality | 2nd Generation Hair Loss |
|---|---|---|---|---|---|---|
| DHNB mg/kg | 100 | Normal | Normal | None | N/A | None |
| | 200 | Normal | Normal | None | N/A | None |
| | 500 | Normal | Normal | None | None | None |
| Allopurinol 500 mg/kg | | Normal for survivors | N/A | Average 42% | Average 42% | 1st batch, 100% 2nd batch, 50% 3rd batch, 20% |

Example 6

XO Inhibition Assay

The procedure of XO inhibition assays is as described in Example 1.

Figure 15A:
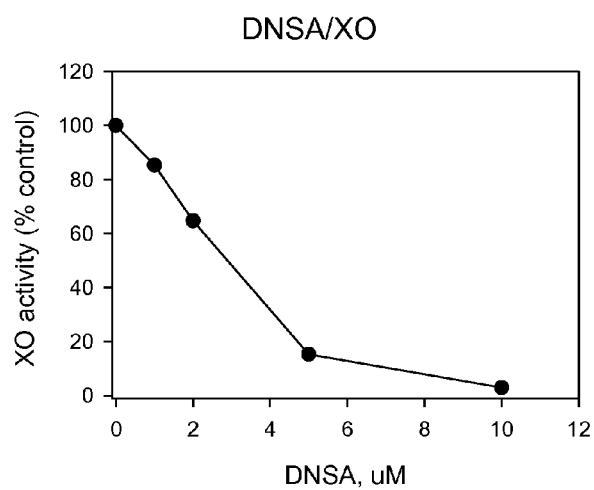
FIGS. 15A and 15B are graphs showing the inhibitory effects of DNSA and NHBA, respectively, on XO activity by measuring the initial rate of uric acid formation.
Figure 15B:
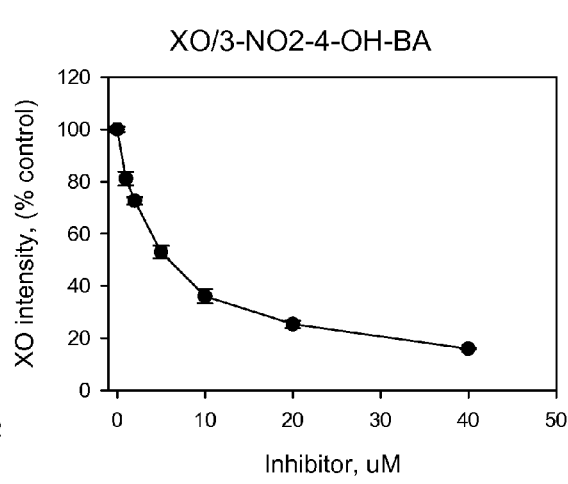

The inhibitory effects of DNSA and NHBA on XO activity were determined by measuring the initial rate of formation of uric acid. Following exposure of XO (5 milliunits/ml) to a 0-10 μM concentration of DNSA or a 0-40 μM concentration of NHBA in 33 mM phosphate buffer (pH 7.4, 25° C.), XO activity was determined by the production of uric acid (295 nm). Reactions were initiated by the addition of xanthine (50 μM). The results are shown in FIGS. 15A and 15B.

Figure 16:
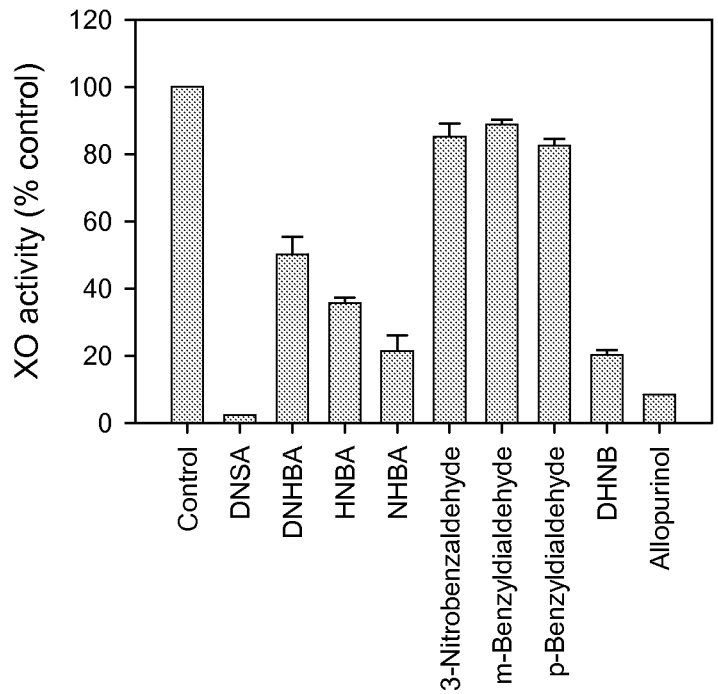
FIG. 16 is a graph comparing the xanthine oxidase inhibitory effects of catechol compounds at a concentration of 20 μM. The control represents no inhibitor added.

The XO inhibition effects of the tested compounds were compared at a concentration of 20 μM. XO activity was determined by measuring the initial rate of formation of uric acid ($\lambda$=295 nm) as in FIGS. 15A-B. After pre-incubation of 20 nM XO and 20 μM inhibitor for 10 min, 50 μM xanthine was added to initiate the reaction. Data represent the mean±S.E. of at least three independent determinations and are shown in FIG. 16.

Figure 17:
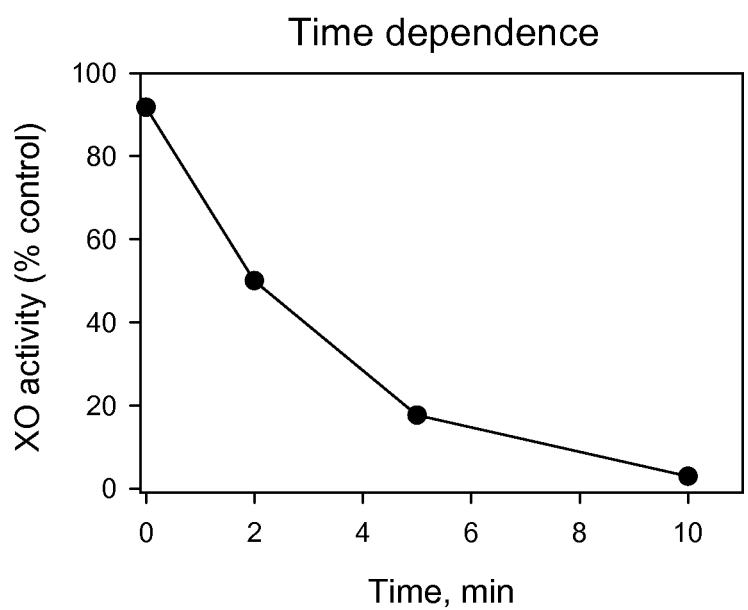
FIG. 17 is a graph demonstrating the influence of pre-incubation of DNSA with XO on XO activity.

The influence of pre-incubation of DNSA with XO on the XO activity was determined. XO activity was determined by the steady-state rate of formation of uric acid ($\lambda$=295 nm) by pre-incubation of 20 nM XO and 20 μM DNSA for 0-10 min followed by the addition of 50 μM xanthine to start the reaction. Data represent one of three independent determinations for DNSA. Pre-incubation of DNSA with XO strongly inhibited XO activity. The results are shown in FIG. 17.

Figure 18:
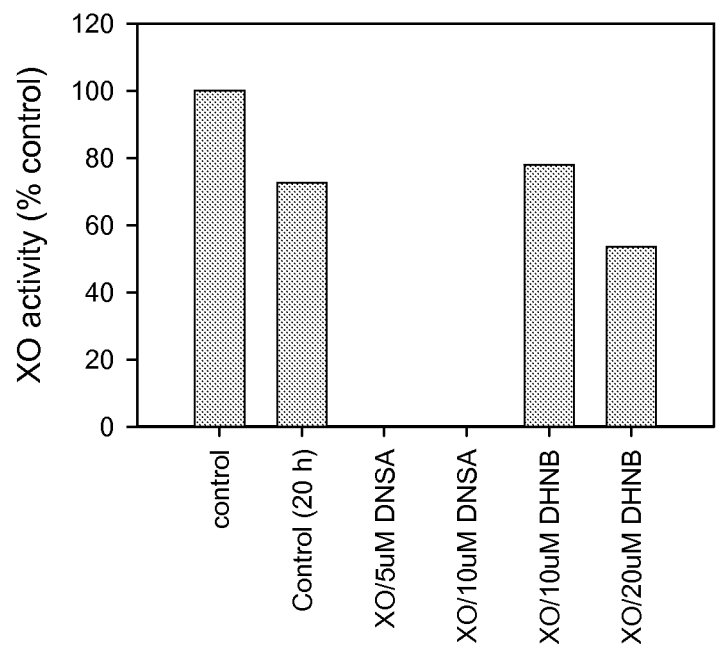
FIG. 18 is a graph demonstrating XO activity after pre-incubation with inhibitors DNSA and DHNB for 20 hours.

The XO activities after pre-incubation with DNSA and DHNB for 20 h were determined. XO stored at room temperature for 20 h decayed in 30% activity, but XO/DNSA (5 μM or 10 μM) samples showed no XO activity at all and DNSA was not converted. For XO/DHNB samples, XO activity was recovered, and DHNB was converted to DHNB-COOH completely. The results are shown in FIG. 18.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims.

Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method for reducing uric acid and/or reactive oxygen species production in a patient in need thereof, comprising administering to the patient an effective amount of compound of Formula III:

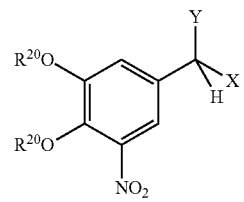

III or a tautomer, a pharmaceutically acceptable salt and/or solvate thereof, where X and Y are independently selected from the group consisting of —OR$^3$, —SR$^3$, —NHR$^3$, and —NHOR$^3$, or X and Y are joined together to form =O, =S, =NR$^3$, =NOR$^3$ or a cyclic ring system of the formula:

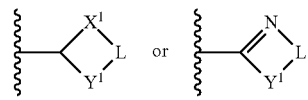

where X$^1$ and Y$^1$ are independently selected from the group consisting of —O—, —S—, —SO$_2$—, and —N(R$^3$)—, and L is —C(O)— or C$_2$ to C$_4$ alkylene group optionally substituted with one or two oxo; and each R$^{20}$ is independently selected from the group consisting of hydrogen, —C(=O)R$^4$, —C(=O)NHR$^4$, —C(=S)R$^4$, —C(=S)NHR$^4$, —C(=O)OR$^4$, —C(=O)SR$^4$, —C(=S)OR$^4$, —P(=O)R$^4$, —P(=O)$_2$ R$^4$, —P(=O)NHR$^4$, —P(=O)$_2$NHR$^4$, —P(=S)NHR$^4$, —P(=O)OR$^4$, —P(=O)$_2$OR$^4$, —P(=O)SR$^4$, —P(=O)$_2$SR$^4$, and —P(=S)OR$^4$, wherein R$^4$ is selected from the group consisting of hydrogen, C$_1$-C$_6$ alkyl, C$_1$-C$_6$ alkoxy, C$_3$-C$_7$ cycloalkyl, C$_2$-C$_6$ alkenyl, C$_4$-C$_7$ cycloalkenyl, C$_2$-C$_6$ alkynyl, C$_6$-C$_{10}$ aryl, and C$_5$-C$_6$ heteoaryl or heterocycle having 1 to 3 heteroatoms selected from O, S, SO$_2$, N, NR$^{11}$, and R$^{30}$; or —OR$^4$ is a hydroxy group esterified with a phospholipid; where is hydrogen or C$_1$ to C$_6$ alkyl, or C$_5$-C$_6$ heteroaryl having 1 to 3 heteroatoms selected from O, S, SO$_2$, N, and NR$^{12}$; R$^{12}$ is hydrogen or C$_1$ to C$_6$ alkyl; and R$^{30}$ is a saturated fatty chain or an unsaturated fatty chain.

2. The method of claim 1, wherein the compound of Formula III is selected from the group consisting of:

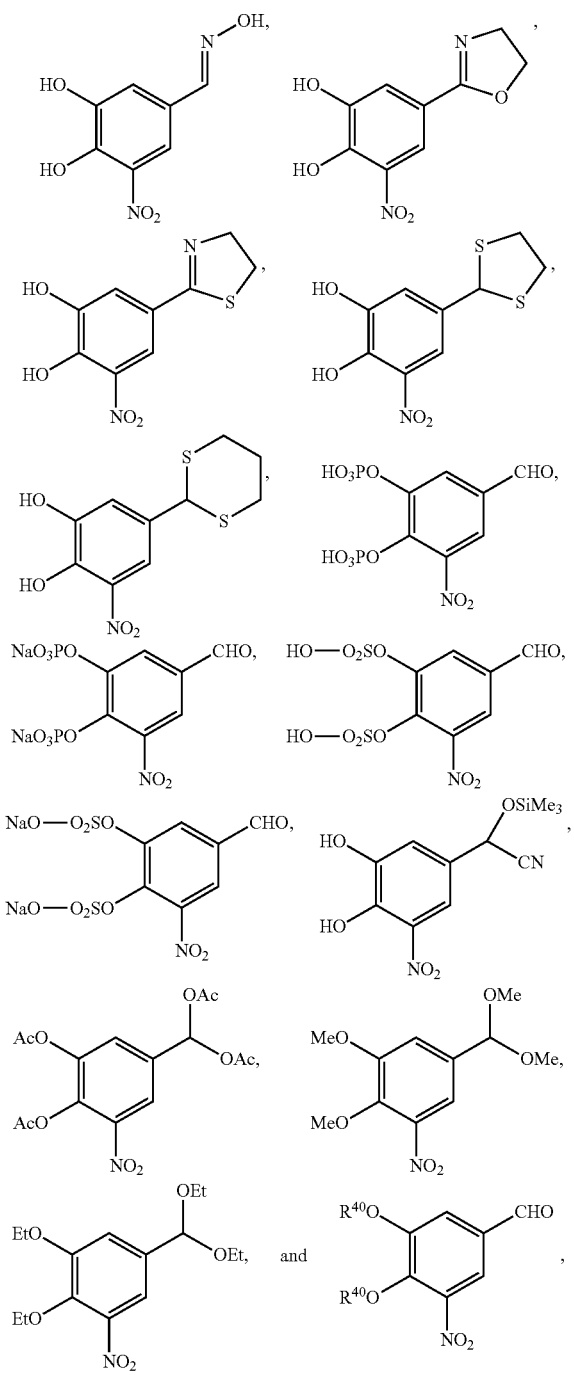

where R⁴⁰ is hydrogen, R³⁰ or —COR³⁰, and where R³⁰, X and Y are defined as in claim 1;
or a tautomer, and/or a pharmaceutically acceptable salt and/or solvate thereof.

3. The method of claim 1, wherein the compound of Formula III is selected from the group consisting of:
   5-(1,3-dioxolan-2-yl)-3-nitrobenzene-1,2-diol;
   3,4-bis(allyloxy)-5-nitrobenzaldehyde;
   and 7-nitro-2-oxobenzo[d][1,3]dioxole-5-carbaldehyde;
or a tautomer, and/or a pharmaceutically acceptable salt and/or solvate thereof.

4. A method for treating a condition, mediated at least in part by xanthine oxidase, in a patient in need thereof, comprising administering to the patient an effective amount of a compound of Formula III:

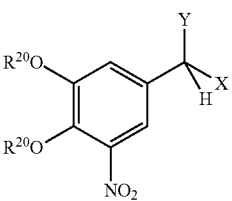

III or a tautomer, a pharmaceutically acceptable salt and/or solvate thereof, where X and Y are independently selected from the group consisting of —OR³, —SR³, —NHR³, and —NHOR³ or X and Y are joined together to form =O, =S, =NR³, =NOR³ or a cyclic ring system of the formula:

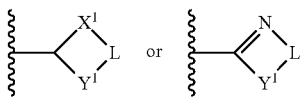

where X¹ and Y¹ are independently selected from the group consisting of —O—, —S—, —SO₂—, and —N(R³)—, and L is —C(O)— or C₂ to C₄ alkylene group optionally substituted with one or two oxo; and each R²⁰ is independently selected from the group consisting of hydrogen, —C(=O)R⁴, —C(=O)NHR⁴, —C(=S)R⁴, —C(=S)NHR⁴, —C(=O)OR⁴, —C(=O)SR⁴, —C(=S)OR⁴, —P(=O)R⁴, —P(=O)₂R⁴, —P(=O)NHR⁴, —P(=O)₂NHR⁴, —P(=S)NHR⁴, —P(=O)OR⁴, —P(=O)₂OR⁴, —P(=O)SR⁴, —P(=O)₂SR⁴, and —P(=S)OR⁴, wherein R⁴ is selected from the group consisting of hydrogen, C₁-C₆ alkyl, C₁-C₆ alkoxy, C₃-C₇ cycloalkyl, C₂-C₆ alkenyl, C₄-C₇ cycloalkenyl, C₂-C₆ alkynyl, C₆-C₁₀ aryl, and C₅-C₆ heteoaryl or heterocycle having 1 to 3 heteroatoms selected from O, S, SO₂, N, NR¹¹, and R³⁰; or —OR⁴ is a hydroxy group esterified with a phospholipid; where R¹¹ is hydrogen or C₁ to C₆ alkyl, or C₅-C₆ heteroaryl having 1 to 3 heteroatoms selected from O, S, SO₂, N, and NR¹²; R¹² is hydrogen or C₁ to C₆ alkyl; and R³⁰ is a saturated fatty chain or an unsaturated fatty chain.

5. The method of claim 4, wherein the compound of Formula III is selected from the group consisting of:

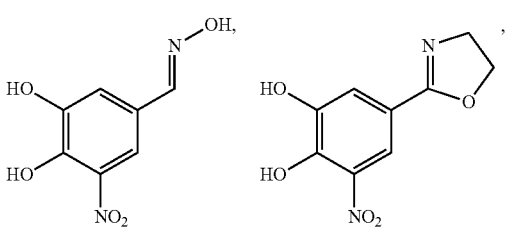

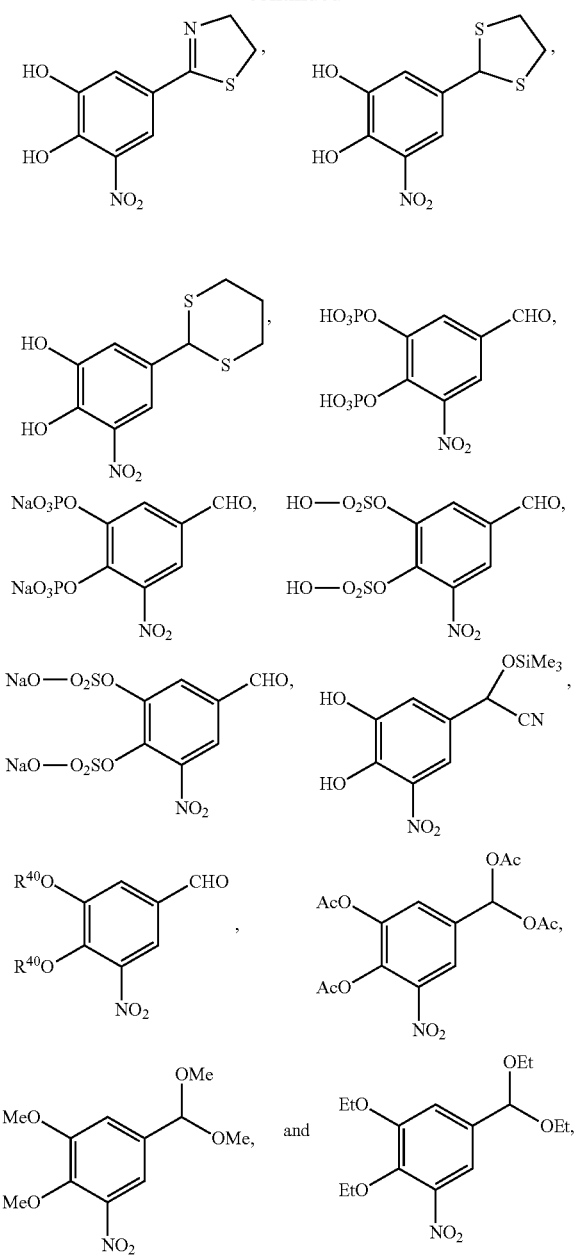

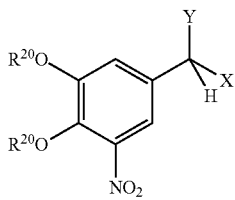

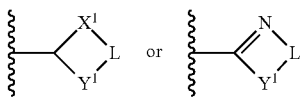

where $R^{40}$ is hydrogen, $R^{30}$ or —$COR^{30}$, and where $R^{30}$, X and Y are defined as in claim 4;

or a tautomer, and/or a pharmaceutically acceptable salt and/or solvate thereof.

6. The method of claim 4, wherein the compound of Formula III is selected from the group consisting of:

5-(1,3-dioxolan-2-yl)-3-nitrobenzene-1,2-diol;

3,4-bis(allyloxy)-5-nitrobenzaldehyde;

and 7-nitro-2-oxobenzo[d][1,3]dioxole-5-carbaldehyde;

or a tautomer, and/or a pharmaceutically acceptable salt and/or solvate thereof.

7. A method for treating hyperuricemia in a patient in need thereof, comprising administering to the patient an effective amount of a compound of Formula III:

III $$R^{20}O \underset{R^{20}O}{\overset{}{\bigcirc}} \overset{Y}{\underset{H}{\overset{}{\bigvee}}} X$$
$$\underset{NO_2}{}$$

or a tautomer, a pharmaceutically acceptable salt and/or solvate thereof, where X and Y are independently selected from the group consisting of —$OR^3$, —$SR^3$, —$NHR^3$, and —$NHOR^3$ or X and Y are joined together to form =O, =S, =$NR^3$, =$NOR^3$ or a cyclic ring system of the formula:

where $X^1$ and $Y^1$ are independently selected from the group consisting of —O—, —S—, —$SO_2$—, and —$N(R^3)$—, and L is —C(O)— or $C_2$ to $C_4$ alkylene group optionally substituted with one or two oxo; and each $R^{20}$ is independently selected from the group consisting of hydrogen, —C(=O)$R^4$, —C(=O)$NHR^4$, —C(=S)$R^4$, —C(=S)$NHR^4$, —C(=O)$OR^4$, —C(=O)$SR^4$, —C(=S)$OR^4$, —P(=O)$R^4$, —P(=O)$_2$ $R^4$, —P(=O)$NHR^4$, —P(=O)$_2NHR^4$, —P(=S)$NHR^4$, —P(=O)$OR^4$, —P(=O)$_2OR^4$, —P(=O)$SR^4$, —P(=O)$_2SR^4$, and —P(=S)$OR^4$, wherein $R^4$ is selected from the group consisting of hydrogen, $C_1$-$C_6$ alkyl, $C_1$-$C_6$ alkoxy, $C_3$-$C_7$ cycloalkyl, $C_2$-$C_6$ alkenyl, $C_4$-$C_7$ cycloalkenyl, $C_2$-$C_6$ alkynyl, $C_6$-$C_{10}$ aryl, and $C_5$-$C_6$ heteoaryl or heterocycle having 1 to 3 heteroatoms selected from O, S, $SO_2$, N, $NR^{11}$, and $R^{30}$ ; or —OR is a hydroxy group esterified with a phospholipid; where $R^{11}$ is hydrogen or $C_1$ to $C_6$ alkyl, or $C_5$-$C_6$ heteroaryl having 1 to 3 heteroatoms selected from O, S, $SO_2$, N, and $NR^{12}$; $R^{12}$ is hydrogen or $C_1$ to $C_6$ alkyl; and $R^{30}$ is a saturated fatty chain or an unsaturated fatty chain.

8. The method of claim 7, wherein the compound of Formula III is selected from the group consisting of:

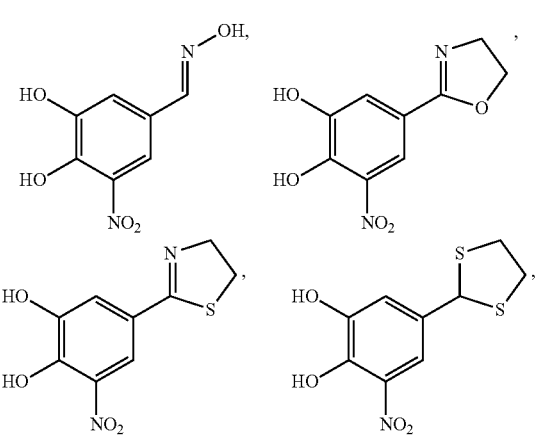

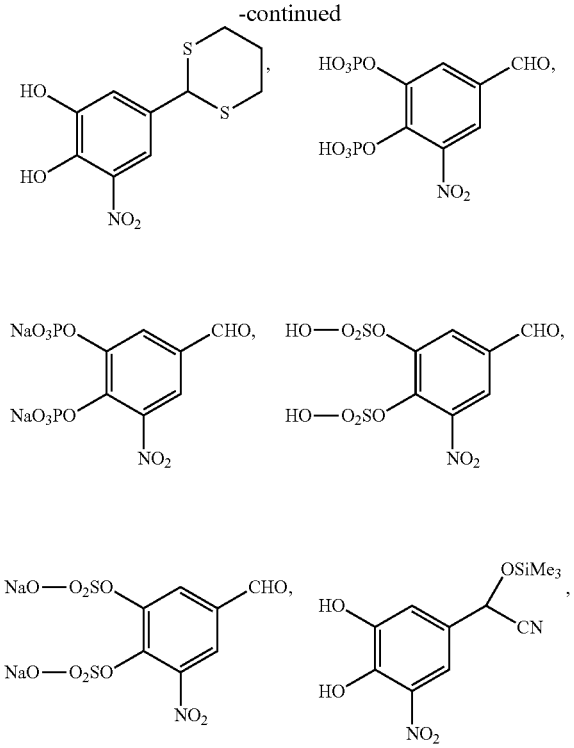
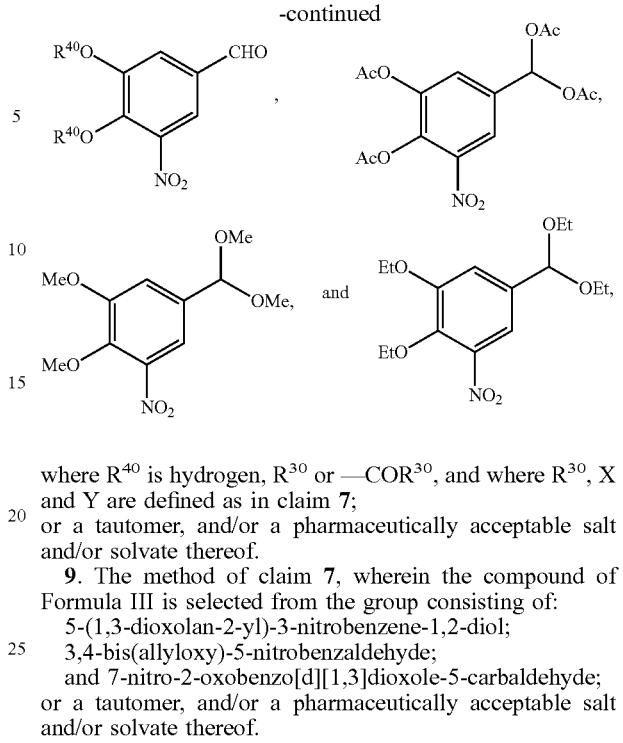

where $R^{40}$ is hydrogen, $R^{30}$ or —$COR^{30}$, and where $R^{30}$, X and Y are defined as in claim 7;
or a tautomer, and/or a pharmaceutically acceptable salt and/or solvate thereof.

9. The method of claim 7, wherein the compound of Formula III is selected from the group consisting of:
5-(1,3-dioxolan-2-yl)-3-nitrobenzene-1,2-diol;
3,4-bis(allyloxy)-5-nitrobenzaldehyde;
and 7-nitro-2-oxobenzo[d][1,3]dioxole-5-carbaldehyde;
or a tautomer, and/or a pharmaceutically acceptable salt and/or solvate thereof.

* * * * *